(12) United States Patent
Carlier et al.

(10) Patent No.: US 8,129,428 B2
(45) Date of Patent: Mar. 6, 2012

(54) INSECTICIDAL CARBAMATES EXHIBITING SPECIES-SELECTIVE INHIBITION OF ACETYLCHOLINESTERASE (ACHE)

(75) Inventors: Paul Carlier, Blacksburg, VA (US); Jeffrey Bloomquist, Blacksburg, VA (US); Sally Paulson, Blacksburg, VA (US); Eric Wong, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 732 days.

(21) Appl. No.: 12/209,301

(22) Filed: Sep. 12, 2008

(65) Prior Publication Data
US 2009/0068242 A1    Mar. 12, 2009

Related U.S. Application Data

(60) Provisional application No. 60/971,614, filed on Sep. 12, 2007, provisional application No. 61/034,260, filed on Mar. 6, 2008.

(51) Int. Cl.
*A01N 47/10* (2006.01)
*C07C 271/00* (2006.01)
(52) U.S. Cl. ........................... 514/491; 560/163
(58) Field of Classification Search ................ None
See application file for complete search history.

(56) References Cited

U.S. PATENT DOCUMENTS
6,509,298 B2    1/2003    Kubota
2004/0004210 A1*    1/2004    Bauer et al. ............ 256/32

FOREIGN PATENT DOCUMENTS
KR    10-20020079339 A    10/2002

OTHER PUBLICATIONS

Mosquito News. "Contact Toxicity of Insecticide Deposits on Filter Paper to Adult Mosquitoes," Jun. 1965, vol. 25, No. 2, pp. 204-208 (Georghiou et al.).
Journal of Labelled Compounds and Radiopharmaceuticals, Apr. 1997 vol. XXXIX, No. 8, pp. 651-668 (Ciszewska et al.).
International Search Report and Written Opinion, PCT/US2008/076108, Apr. 30, 2009.
Carbamate Insecticides, Some Structural Relationships of a Group of Simple Alkyl Phenyl N-Methylcarbambates to Anticholinesterase Activity, J. Agr. Food Chem., vol. 13, No. 3, May-Jun. 1965, pp. 232-235 (Kohn et al.).
Insecticide Structure and Activity, Insecticidal Activity of Carbamate Cholinesterase Inhibitors, J. Agr. and Food Chem., vol. 2, No. 17, Aug. 18, 1954, pp. 864-870 (Kolbezen et al.).
Structure-Activity Relationships for Insecticidal Carbamates, Bull. Wld. Hlth. Org., vol. 44, pp. 43-78, 1971 (Metcalf).
Carbamate Insecticides, Effects of Chemical Structure on Intoxication and Detoxication of Phenyl N-Methylcarbamates in Insects, J. Agr. Food Chem., vol. 13, No. 3, May-Jun. 1965, pp. 220-231 (Metcalf et al.).
Acetylcholinesterase Inhibition by Substituted Phenyl N-Alkyl Carbamates, J. Agr. Food Chem., vol. 20, No. 3, 1972, pp. 537-540 (Yu et al.).
Silicon-containing carbamate insecticides, J. Econ. Ent., 1965, vol. 58 1151 (Metcalf et al.).
International Preliminary Report on Patentability, PCT/US2008/076108, Mar. 16, 2010.
Singapore Written Opinion of Application 201001694-7, dated Apr. 15, 2011.
Hadaway, A. B.; Barlow, F. The Relative Toxicity to Adult Mosquitos of Derivatives of Phenyl N-Methylcarbamate. Bulletin of the World Health Organization. 1965, 32, 581-585.

* cited by examiner

*Primary Examiner* — Paul A Zucker
(74) *Attorney, Agent, or Firm* — New River Valley IP Law; Michele L. Mayberry

(57) ABSTRACT

The present invention includes insecticidal carbamates that are useful, for example, for the control of insects, such as mosquitoes, which can be used in applications where exposure to and/or contact with humans is likely. The insecticides of the present invention include phenyl N-methyl carbamates and compositions comprising them that exhibit species-selective inhibition of acetylcholinesterase (AChE) and are preferably toxic to mosquitoes but not humans. Of particular interest are compounds of Formula (I) and Formula (II):

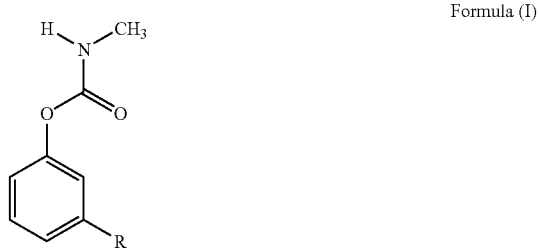

Formula (I)

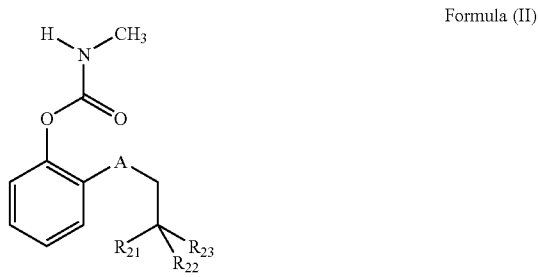

Formula (II)

Compounds of Formula (I) and Formula (II) are especially suitable for insecticide treated nets and indoor residual spraying for mosquito control.

12 Claims, 3 Drawing Sheets

Figure 3. Residual AChE activity vs carbamate concentration for 1b (left) and 2b (right)

US 8,129,428 B2

INSECTICIDAL CARBAMATES EXHIBITING SPECIES-SELECTIVE INHIBITION OF ACETYLCHOLINESTERASE (ACHE)

CROSS-REFERENCE TO RELATED APPLICATIONS

This application relies on the disclosure and claims the benefit of the filing date of U.S. Provisional Application No. 60/971,614 filed Sep. 12, 2007 and U.S. Provisional Application No. 61/034,260 filed Mar. 6, 2008, the disclosures of which are incorporated herein by reference in their entireties.

STATEMENT OF GOVERNMENT INTEREST

This invention was funded in part by a Grant from the Foundation for the National Institutes of Health, Inc. through the Grand Challenges in Global Health initiative, with funds provided by the Bill & Melinda Gates Foundation. The Foundation for the National Institutes of Health was established by the United States Congress to support the mission of the National Institutes of Health—improving health through scientific discovery. The Foundation identifies and develops opportunities for innovative public-private partnerships involving industry, academia, and the philanthropic community. A non-profit, 501(c)(3) corporation, the Foundation raises private-sector funds for a broad portfolio of unique programs that complement and enhance NIH priorities and activities.

BACKGROUND OF THE INVENTION

1. Field of the Invention

The present invention relates to the fields of chemistry and biology and more particularly to the field of insecticides. The present invention includes insecticidal carbamates that are useful, for example, for the control of insects, such as mosquitoes, which can be used in applications where exposure to and/or contact with humans is likely. The insecticides of the present invention exhibit species-selective inhibition of acetylcholinesterase (AChE) and are toxic to mosquitoes but not humans.

2. Description of Related Art

Malaria is a global scourge. Over three billion people are at risk of infection by the malaria parasites *Plasmodium falciparum* and *Plasmodium vivax*, which cause an estimated one to two million deaths annually. For many in sub-Saharan Africa, especially children, insecticide treated nets (ITNs) provide the only means of defense against *Anopheles gambiae*, the mosquito vector of the parasites. Carbamate insecticides work by inhibiting acetylcholinesterase (AChE), and are commonly used to control agricultural pests and disease vectors. Human toxicity (resulting from concurrent potent inhibition of human AChE), however, has thus far discouraged deployment of insecticidal carbamates on ITNs. Currently, pyrethroid insecticides have filled this gap. It would thus be desirable to improve current ITN performance by identifying classes of carbamates that possess excellent target selectivity for *Anopheles gambaie* AChE (AgAChE) over human AChE (hAChE). Such highly selective carbamates would be ideally suited for safe deployment on ITNs, but up to the inventors' work in this area such compounds have been unavailable. The present inventors have identified certain carbamates that are much more potent at AgAChE than at hAChE. This difference in potency for the two species is unanticipated and potentially very useful.

Of carbamates, 3-tert-butylphenyl-N-methyl carbamate (carbamate 1a) has been studied extensively and is known commercially by the name "terbam." Kolbezen et al. reported that 3-tert-butylphenyl-N-methyl carbamate was a 400 nM inhibitor of *Musca domestica* (i.e., housefly) AChE (MdAChE) and that it was significantly toxic to houseflies upon topical administration ($LD_{50}$ 50 mg/kg). (Kolbezen, M.J.; Metcalf, R.L.; Fukuto, T.R. Insecticide Structure and Activity, Insecticidal Activity of Carbamate Cholinesterase Inhibitors. *J. Agric. Food Chem.* 1954, 2, 864-870.) Subsequent studies by Kohn showed carbamate 1a to have similar potency at bovine AChE (530 nM). (Kohn, G. K.; Ospenson, J. N.; Moore, J. E. Carbamate Insecticides, Some Structural Relationships of a Group of Simple Alkyl Phenyl N-Methyl-carbamates to Anticholinesterase Activity. *J. Agric. Food Chem.* 1965, 13, 232-235.) Indeed, in his massive review, Metcalf noted that the few bovine AChE $IC_{50}$ values reported at that time matched MdAChE $IC_{50}$ values well. (Metcalf, R. L. Structure-Activity Relationships for Insecticidal Carbamates. *Bull. Wld Hlth Org.* 1971, 44, 43-78.) The present inventors found that the hAChE $IC_{50}$ for carbamate 1a (265 nM) is within a factor of 2 of that reported by Kohn for bovine AChE. Thus, previous data tended to support that carbamates, e.g., 3-tert-butylphenyl-N-methyl carbamate (carbamate 1a), that are toxic to houseflies are expected to be toxic to bovine and humans.

To the contrary, however, the present inventors have identified certain carbamates that are much more potent at AgAChE than at MdAChE. This difference in potency for the two insect species is unanticipated and leads to high selectivity for AgAChE relative to hAChE.

SUMMARY OF THE INVENTION

The present invention addresses at least some of the needs discussed above by providing carbamate insecticides that can be used in close proximity to humans. In particular, the present invention provides phenyl N-methyl carbamates that are lethal to insects, including mosquitoes. Preferred phenyl N-methyl carbamates and compositions of the present invention include compounds that are lethal to insects, including mosquitoes, but that are not lethal to humans, including when applied in appropriate doses.

The present invention includes N-methyl carbamates of Formulas (I) and (II):

Formula (I)

Formula (II)

With respect to the compounds of Formula (I):

R is chosen from $C(R_1)(R_2)(R_3)$ and $Si(R_1)(R_2)(R_3')$, wherein $R_1$ is chosen from methyl, ethyl, n-alkyl ($C_3$-$C_{10}$), —$(CH_2)_n$-aryl, —$CF_3$, and —$CF_2CF_3$, wherein n is 0 to 10 and aryl is chosen from phenyl, 1-naphthyl, and 2-naphthyl, each of which is unsubstituted or substituted with three or fewer substituents chosen from bromo, carboethoxy, carbomethoxy, chloro, cyano, ethoxy, ethyl, fluoro, iodo, isopropoxy, isopropyl, methoxy, methyl, nitro, thioethyl, thioisopropyl, and thiomethyl;

$R_2$ is chosen from methyl, ethyl, n-alkyl ($C_3$-$C_{10}$), branched ($C_3$-$C_{10}$) alkyl, —$(CH_2)_n$-aryl, —$CF_3$, and —$CF_2CF_3$, wherein n and aryl are as defined above;

$R_3$ is chosen from methyl, ethyl, n-alkyl ($C_3$-$C_{10}$), halogen (fluoro, chloro, bromo, and iodo), —$CF_3$, —$CF_2CF_3$, $OR_4$, $C(O)R_4$, $C(O)OR_4$, and $C(O)NR_4R_5$, wherein $R_4$ is chosen from methyl, ethyl, n-alkyl or branched alkyl ($C_3$-$C_{10}$), and —$(CH_2)_n$-aryl, wherein n and aryl are as defined above, and $R_5$ is chosen from hydrogen, methyl, and ethyl; and $R_3'$ is chosen from methyl, ethyl, n-alkyl ($C_3$-$C_{10}$), halogen (fluoro, chloro, bromo, and iodo), and $OR_4$, wherein $R_4$ is as defined above.

For example, substituents for the substituted aryl group identified above with respect to Formula (I) include —Br, —$CO_2CH_2CH_3$, —$CO_2CH_3$, —Cl, —CN, —$OCH_2CH_3$, —$CH_2CH_3$, —F, —I, —Oi-Pr, -i-Pr, —$OCH_3$, —$CH_3$, —$NO_2$, —$SCH_2CH_3$, —Si—Pr, and —$SCH_3$. Also, as described above with respect to Formula (I), three or fewer of such substituents can be present on the phenyl, 1-naphthyl, or 2-naphthyl, meaning that the aryl can be unsubstituted (i.e., comprising hydrogen) or substituted with up to and including three substituents. The substituents can be distributed at any position of the aryl and, in the case of 1-naphthyl or 2-naphthyl, the substituents can be distributed at any position of either of the naphthyl rings. Further, the "1-" or "2-" of the naphthyl refers to the position of the naphthyl ring where the naphthyl attaches to the remainder of the compound. For example, 1-naphthyl and 2-naphthyl refer to the following:

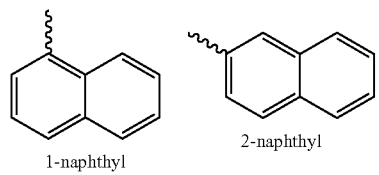

1-naphthyl     2-naphthyl

Of particular interest are compounds of Formula (I) chosen from N-methyl 3-(tert-butyl)phenyl carbamate, N-methyl 3-(ethyldimethylsilyl)phenyl carbamate, and N-methyl 3-(trimethylsilyl)phenyl carbamate.

With respect to the compounds of Formula (II):

A is chosen from O and S;

$R_{21}$ is chosen from methyl, ethyl, propyl, isopropyl, butyl, sec-butyl, isobutyl, —$CF_3$, —$CF_2CF_3$, =$CH_2$, =$CHCH_3$, =$CHCH_2CH_3$, =$C(CH_3)_2$, =$CHCH_2CH_2CH_3$, and =$C(CH_3)(CH_2CH_3)$;

$R_{22}$ is chosen from methyl, ethyl, propyl, butyl, —$CF_3$, and —$CF_2CF_3$; and $R_{23}$ is hydrogen or when appropriate is no substituent.

The N-methyl carbamates of Formula (II) of the present invention include, for chiral compounds, racemates and enantiomers, and when $R_{21}$ is chosen from =$CHCH_3$, =$CHCH_2CH_3$, =$CHCH_2CH_2CH_3$, and =$C(CH_3)(CH_2CH_3)$, E and Z stereoisomers and mixtures.

Of particular interest are compounds of Formula (II), wherein $R_{21}$ and $R_{22}$ are chosen from methyl and ethyl, and $R_{23}$ is hydrogen, or wherein $R_{21}$ is =$CH_2$, $R_{22}$ is methyl, and there is no $R_{23}$. For example, as discussed in further detail below, of particular interest are the following compounds, which exhibit highly potent and selective AgAChE inhibition: (1b) 2-(2-ethylbutylthio)phenyl-N-methylcarbamate; (2b) 2-(2-ethylbutoxy)phenyl-N-methylcarbamate; (4b) 2-(2-methylbutylthio)phenyl-N-methylcarbamate; (6b) 2-(isobutylthio)phenyl-N-methylcarbamate; (8b) 2-(2-methylallylthio)phenyl-N-methylcarbamate; and (13b) 2-isobutoxyphenyl-N-methylcarbamate.

The present invention further includes methods of preparing compounds of Formula (I) comprising: (a) deprotonating a phenol with K(Ot-Bu) or NaH in THF to obtain a deprotonated phenol; (b) carbamoylating said deprotonated phenol by reacting said deprotonated phenol with N-methyl carbamoyl chloride; and (c) isolating the resultant compound to obtain a compound of Formula (I). Methods of preparing compounds of Formula (II) are also included within the invention, which comprise: (a) deprotonating a phenol with K(Ot-Bu) in THF to obtain a deprotonated phenol; (b) carbamoylating said deprotonated phenol by reacting said deprotonated phenol with N-methylcarbamoyl chloride; and (c) isolating the resultant compound to obtain a compound of Formula (II).

Further provided by the present invention are methods of controlling mosquitoes comprising applying a compound of Formula (I) and/or Formula II to a substrate and exposing the substrate to mosquitoes for a time sufficient to kill the mosquitoes. The substrate can be any solid support, including that of an agricultural or residential nature. The compounds can be applied to crops, trees, walls, and nets to name a few.

Also included within the invention are insecticidal compositions and insecticide treated nets comprising a compound of Formula (I) or Formula (II). Such compositions and substrates can further comprise a synergist to increase the lethality of the compounds, such as piperonyl butoxide. Even further, the insecticidal compositions and insecticide treated nets can comprise one or more of the compounds of Formula (I) and/or Formula (II).

DETAILED DESCRIPTION OF VARIOUS EMBODIMENTS OF THE INVENTION

Figure 1:
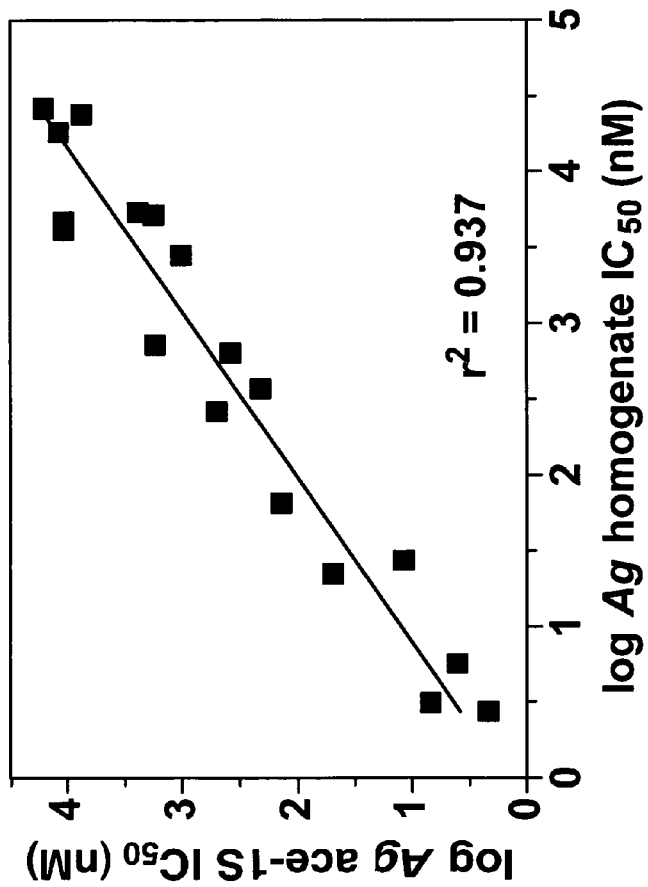
FIG. 1 is a graph showing a plot of log(Ag ace-1S $IC_{50}$ (nM)) vs log(Ag hmg $IC_{50}$ (nM)) for the commercial and synthesized inhibitors described in Tables 1 and 2.

Reference will now be made in detail to various exemplary embodiments of the invention. It is to be understood that the following detailed description is presented for the purpose of describing certain embodiments in detail. Thus, the following detailed description is not to be considered as limiting the invention to the embodiments described. Rather, the true scope of the invention is defined by the claims.

The present invention includes compounds of Formula (I):

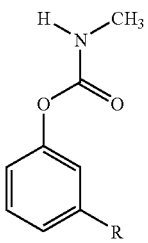

Formula (I)

wherein:

R is chosen from $C(R_1)(R_2)(R_3)$ and $Si(R_1)(R_2)(R_3')$, wherein $R_1$ is chosen from methyl, ethyl, n-alkyl ($C_3$-$C_{10}$), —$(CH_2)_n$-aryl, —$CF_3$, and —$CF_2CF_3$, wherein n is 0 to 10 and aryl is chosen from phenyl, 1-naphthyl, and 2-naphthyl, each of which is unsubstituted or substituted with three or fewer substituents chosen from bromo, carboethoxy, carbomethoxy, chloro, cyano, ethoxy, ethyl, fluoro, iodo, isopropoxy, isopropyl, methoxy, methyl, nitro, thioethyl, thioisopropyl, and thiomethyl;

$R_2$ is chosen from methyl, ethyl, n-alkyl ($C_3$-$C_{10}$), branched ($C_3$-$C_{10}$) alkyl, —$(CH_2)_n$-aryl, —$CF_3$, and —$CF_2CF_3$, wherein n and aryl are as defined above;

$R_3$ is chosen from methyl, ethyl, n-alkyl ($C_3$-$C_{10}$), fluoro, chloro, bromo, iodo, —$CF_3$, —$CF_2CF_3$, $OR_4$, $C(O)R_4$, $C(O)OR_4$, and $C(O)NR_4R_5$, wherein $R_4$ is chosen from methyl, ethyl, n-alkyl or branched alkyl ($C_3$-$C_{10}$), and —$(CH_2)_n$-aryl, wherein n and aryl are as defined above, and $R_5$ is chosen from hydrogen, methyl, and ethyl; and $R_3'$ is chosen from methyl, ethyl, n-alkyl ($C_3$-$C_{10}$), fluoro, chloro, bromo, iodo, and $OR_4$, wherein $R_4$ is as defined above.

Methods of making compounds of Formula (I) are also included in the present invention, wherein the methods comprise:

deprotonating a phenol with K(Ot-Bu) or NaH in THF to obtain a deprotonated phenol;

carbamoylating said deprotonated phenol by reacting said deprotonated phenol with N-methyl carbamoyl chloride; and isolating the resultant compound to obtain a compound of Formula (I):

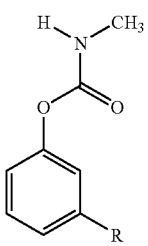

Formula (I)

wherein:

R is chosen from $C(R_1)(R_2)(R_3)$ and $Si(R_1)(R_2)(R_3')$, wherein $R_1$ is chosen from methyl, ethyl, n-alkyl ($C_3$-$C_{10}$), —$(CH_2)_n$-aryl, —$CF_3$, and —$CF_2CF_3$, wherein n is 0 to 10 and aryl is chosen from phenyl, 1-naphthyl, and 2-naphthyl, each of which is unsubstituted or substituted with three or fewer substituents chosen from bromo, carboethoxy, carbomethoxy, chloro, cyano, ethoxy, ethyl, fluoro, iodo, isopropoxy, isopropyl, methoxy, methyl, nitro, thioethyl, thioisopropyl, and thiomethyl;

$R_2$ is chosen from methyl, ethyl, n-alkyl ($C_3$-$C_{10}$), branched ($C_3$-$C_{10}$) alkyl, —$(CH_2)_n$-aryl, —$CF_3$, and —$CF_2CF_3$, wherein n and aryl are as defined above;

$R_3$ is chosen from methyl, ethyl, n-alkyl ($C_3$-$C_{10}$), fluoro, chloro, bromo, iodo, —$CF_3$, —$CF_2CF_3$, $OR_4$, $C(O)R_4$, $C(O)OR_4$, and $C(O)NR_4R_5$, wherein $R_4$ is chosen from methyl, ethyl, n-alkyl or branched alkyl ($C_3$-$C_{10}$), and —$(CH_2)_n$-aryl, wherein n and aryl are as defined above, and $R_5$ is chosen from hydrogen, methyl, and ethyl; and $R_3'$ is chosen from methyl, ethyl, n-alkyl ($C_3$-$C_{10}$), fluoro, chloro, bromo, iodo, and $OR_4$, wherein $R_4$ is as defined above.

In the case of compounds of Formula (I) where it is desired to obtain a phenol comprising 2-trifluoromethylpropan-2-yl, 2-trifluoromethylbutan-2-yl, or 3,3,4,4,4-pentafluoro-2-methylbutan-2-yl groups at the C3 position, possible methods of synthesis can include adapting the route of Tanaka et al. (Bioorg. Med. Chem. Lett. 2007, 17, 6079-6085). In brief, 3-hydroxyacetophenone or 3-hydroxypropiophenone is treated with the Rupert-Prakash reagent or its pentafluoroethyl analogue (J. Am. Chem. Soc. 1989, 111, 393-395). The resulting tertiary benzylic alcohol is treated with the Reetz reagent (J. Org. Chem. 1983, 48, 254-255) to effect replacement of the hydroxy group by methyl. Phenols containing the 1,1,1,3,3,3-hexafluoro-2-methylpropan-2-yl and related groups are prepared according to the method of Satake et al (U.S. Pat. No. 6,506,775) or Burton et al. (J. Org. Chem. 1967, 33, 1854-1860). Phenols containing the perfluoro-tert-butyl and other perfluoro tert-alkyl groups are prepared according to the method of Hochlowski et al. (U.S. Pat. No. 6,168,913) or Kalbitzer et al. (NMR in Biomedicine 1992, 5, 347-350). Phenols containing other perfluoroalkyl groups are prepared similarly.

Methods of controlling mosquitoes are also included within the invention, where the methods comprise applying a compound or composition comprising a compound lethal to mosquitoes to a substrate and exposing said substrate to mosquitoes for a time sufficient to kill said mosquitoes, wherein said compound is one or more compounds of Formula (I):

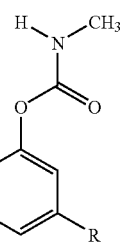

Formula (I)

wherein:

R is chosen from $C(R_1)(R_2)(R_3)$ and $Si(R_1)(R_2)(R_3')$, wherein $R_1$ is chosen from methyl, ethyl, n-alkyl ($C_3$-$C_{10}$), —$(CH_2)_n$-aryl, —$CF_3$, and —$CF_2CF_3$, wherein n is 0 to 10 and aryl is chosen from phenyl, 1-naphthyl, and 2-naphthyl, each of which is unsubstituted or substituted with three or fewer substituents chosen from bromo, carboethoxy, carbomethoxy, chloro, cyano, ethoxy, ethyl, fluoro, iodo, isopropoxy, isopropyl, methoxy, methyl, nitro, thioethyl, thioisopropyl, and thiomethyl;

$R_2$ is chosen from methyl, ethyl, n-alkyl ($C_3$-$C_{10}$), branched ($C_3$-$C_{10}$) alkyl, —$(CH_2)_n$-aryl, —$CF_3$, and —$CF_2CF_3$, wherein n and aryl are as defined above;

$R_3$ is chosen from methyl, ethyl, n-alkyl ($C_3$-$C_{10}$), fluoro, chloro, bromo, iodo, —$CF_3$, —$CF_2CF_3$, $OR_4$, $C(O)R_4$, $C(O)OR_4$, and $C(O)NR_4R_5$, wherein $R_4$ is chosen from methyl, ethyl, n-alkyl or branched alkyl ($C_3$-$C_{10}$), and —$(CH_2)_n$-aryl, wherein n and aryl are as defined above, and $R_5$ is chosen from hydrogen, methyl, and ethyl; and $R_3'$ is chosen from methyl, ethyl, n-alkyl ($C_3$-$C_{10}$), fluoro, chloro, bromo, iodo, and $OR_4$, wherein $R_4$ is as defined above.

The present invention further includes insecticidal compositions comprising one or more compounds of Formula (I):

Formula (I)

wherein:

R is chosen from $C(R_1)(R_2)(R_3)$ and $Si(R_1)(R_2)(R_3')$, wherein $R_1$ is chosen from methyl, ethyl, n-alkyl ($C_3$-$C_{10}$), —$(CH_2)_n$-aryl, —$CF_3$, and —$CF_2CF_3$, wherein n is 0 to 10 and aryl is chosen from phenyl, 1-naphthyl, and 2-naphthyl, each of which is unsubstituted or substituted with three or fewer substituents chosen from bromo, carboethoxy, carbomethoxy, chloro, cyano, ethoxy, ethyl, fluoro, iodo, isopropoxy, isopropyl, methoxy, methyl, nitro, thioethyl, thioisopropyl, and thiomethyl;

$R_2$ is chosen from methyl, ethyl, n-alkyl ($C_3$-$C_{10}$), branched ($C_3$-$C_{10}$) alkyl, —$(CH_2)_n$-aryl, —$CF_3$, and —$CF_2CF_3$, wherein n and aryl are as defined above;

$R_3$ is chosen from methyl, ethyl, n-alkyl ($C_3$-$C_{10}$), fluoro, chloro, bromo, iodo, —$CF_3$, —$CF_2CF_3$, $OR_4$, $C(O)R_4$, $C(O)OR_4$, and $C(O)NR_4R_5$, wherein $R_4$ is chosen from methyl, ethyl, n-alkyl or branched alkyl ($C_3$-$C_{10}$), and —$(CH_2)_n$-aryl, wherein n and aryl are as defined above, and $R_5$ is chosen from hydrogen, methyl, and ethyl; and $R_3'$ is chosen from methyl, ethyl, n-alkyl ($C_3$-$C_{10}$), fluoro, chloro, bromo, iodo, and $OR_4$, wherein $R_4$ is as defined above.

The compounds and compositions are useful for controlling mosquitoes for example when used with a substrate, especially in close proximity to humans. One such substrate for example are nets comprising one or more compounds of Formula (I) or a composition comprising one or more compounds of Formula (I):

Formula (I)

wherein:

R is chosen from $C(R_1)(R_2)(R_3)$ and $Si(R_1)(R_2)(R_3')$, wherein $R_1$ is chosen from methyl, ethyl, n-alkyl ($C_3$-$C_{10}$), —$(CH_2)_n$-aryl, —$CF_3$, and —$CF_2CF_3$, wherein n is 0 to 10 and aryl is chosen from phenyl, 1-naphthyl, and 2-naphthyl, each of which is unsubstituted or substituted with three or fewer substituents chosen from bromo, carboethoxy, carbomethoxy, chloro, cyano, ethoxy, ethyl, fluoro, iodo, isopropoxy, isopropyl, methoxy, methyl, nitro, thioethyl, thioisopropyl, and thiomethyl;

$R_2$ is chosen from methyl, ethyl, n-alkyl ($C_3$-$C_{10}$), branched ($C_3$-$C_{10}$) alkyl, —$(CH_2)_n$-aryl, —$CF_3$, and —$CF_2CF_3$, wherein n and aryl are as defined above;

$R_3$ is chosen from methyl, ethyl, n-alkyl ($C_3$-$C_{10}$), fluoro, chloro, bromo, iodo, —$CF_3$, —$CF_2CF_3$, $OR_4$, $C(O)R_4$, $C(O)OR_4$, and $C(O)NR_4R_5$, wherein $R_4$ is chosen from methyl, ethyl, n-alkyl or branched alkyl ($C_3$-$C_{10}$), and —$(CH_2)_n$-aryl, wherein n and aryl are as defined above, and $R_5$ is chosen from hydrogen, methyl, and ethyl; and $R_3'$ is chosen from methyl, ethyl, n-alkyl ($C_3$-$C_{10}$), fluoro, chloro, bromo, iodo, and $OR_4$, wherein $R_4$ is as defined above.

In accordance with the present invention, N-methyl 3-(ethyldimethylsilyl)phenyl carbamate is a preferred compound of Formula (I). Further, for example, preferred compounds of Formula (I) for compositions according to the invention, as well as for indoor residual spraying and nets and/or other substrates comprising insecticidal carbamates include N-methyl 3-(tert-butyl)phenyl carbamate, N-methyl 3-(ethyldimethylsilyl)phenyl carbamate, and N-methyl 3-(trimethylsilyl)phenyl carbamate. Compounds of Formula (I), wherein $R_1$, $R_2$, and/or $R_3$ comprise a —$CF_3$ or —$CF_2CF_3$ group, may be desirable for increased resistance to oxidative detoxification mechanisms in the insect thus conferring greater toxicity to mosquitoes. Exemplary compounds include 3-(1,1,1-trifluoro-2-methylpropan-2-yl)phenyl N-methylcarbamate; 3-(1,1,1,3,3,3-hexafluoro-2-methylpropan-2-yl)phenyl N-methylcarbamate; 3-(1,1,1,3,3,3-hexafluoro-2-(trifluoromethyl)propan-2-yl)phenyl N-methylcarbamate; 3-(1,1,1-trifluoro-2-methylbutan-2-yl)phenyl N-methylcarbamate; 3-(1,1,1-trifluoro-2-(trifluoromethyl)butan-2-yl)phenyl N-methylcarbamate; 3-(3,3,4,4,4-pentafluoro-2-methylbutan-2-yl)phenyl N-methylcarbamate; 3-(1,1,1,3,3,4,4,4-octafluoro-2-methylbutan-2-yl)phenyl N-methylcarbamate; and 3-(1,1,1,3,3,4,4,4-octafluoro-2-(trifluoromethyl)butan-2-yl)phenyl N-methylcarbamate, for example.

The compounds and compositions comprising one or more compounds of Formula (I) in accordance with the invention can be applied to agricultural substrates, including crops. Further applications that the compounds and compositions of the present invention are useful for include applying one or more compounds of Formula (I) or compositions comprising them in the context of indoor residual spraying or treating of nets.

The methods, compositions, substrates, and nets according to the invention can comprise a synergist for increasing the lethality of a compound of Formula (I), such as for example, piperonyl butoxide.

The present invention further includes compounds of Formula (II):

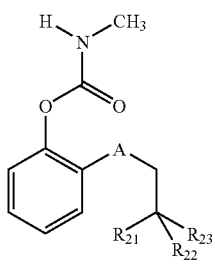

Formula (II)

wherein:

A is chosen from O and S;

$R_{21}$ is chosen from methyl, ethyl, propyl, isopropyl, butyl, sec-butyl, isobutyl, —$CF_3$, —$CF_2CF_3$, =$CH_2$, =$CHCH_3$, =$CHCH_2CH_3$, =$C(CH_3)_2$, =$CHCH_2CH_2CH_3$, and =$C(CH_3)(CH_2CH_3)$;

$R_{22}$ is chosen from methyl, ethyl, propyl, butyl, —$CF_3$, and —$CF_2CF_3$; and $R_{23}$ is hydrogen or when appropriate is no substituent.

Methods of making compounds of Formula (II) are also included in the present invention, wherein the methods comprise:

deprotonating a phenol with K(Ot-Bu) in THF to obtain a deprotonated phenol;

carbamoylating said deprotonated phenol by reacting said deprotonated phenol with N-methylcarbamoyl chloride; and isolating the resultant compound to obtain a compound of Formula (II):

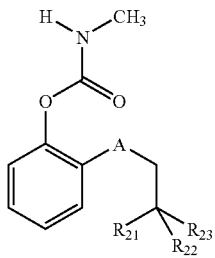

Formula (II)

wherein:

A is chosen from O and S;

$R_{21}$ is chosen from methyl, ethyl, propyl, isopropyl, butyl, sec-butyl, isobutyl, —$CF_3$, —$CF_2CF_3$, =$CH_2$, =$CHCH_3$, =$CHCH_2CH_3$, =$C(CH_3)_2$, =$CHCH_2CH_2CH_3$, and =$C(CH_3)(CH_2CH_3)$;

$R_{22}$ is chosen from methyl, ethyl, propyl, butyl, —$CF_3$, and —$CF_2CF_3$; and $R_{23}$ is hydrogen or when appropriate is no substituent. In the case of compounds of Formula (II) where it is desired to obtain a phenol comprising fluorinated 2-thioalkyl or 2-alkoxy substituents can, for example, be prepared in the following way. 2-perfluoroalkylacrylates and higher homologues are prepared by the method of Yamazaki et al. (Org. Lett. 2001, 3, 2915), which are hydrogenated to give 2-perfluoroalkyl alkanoate esters according to Yamazaki et al. (J. Org. Chem. 2006, 71, 2499). Reduction with lithium aluminum hydride affords the corresponding primary alcohols. These alcohols are converted to the iodide, tosylate or triflate derivatives using standard methods; these electrophiles are used in the standard S-and O-alkylation protocols of 2-mercaptophenol and catechol described in this disclosure to generate the desired phenols.

Methods of controlling mosquitoes are also included within the invention, where the methods comprise applying a compound or composition comprising a compound lethal to mosquitoes to a substrate and exposing said substrate to mosquitoes for a time sufficient to kill said mosquitoes, wherein said compound is one or more compounds of Formula (II):

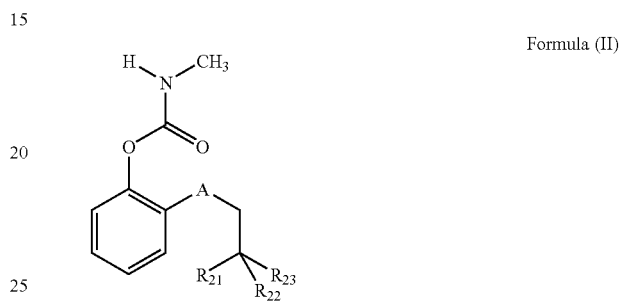

Formula (II)

wherein:

A is chosen from O and S;

$R_{21}$ is chosen from methyl, ethyl, propyl, isopropyl, butyl, sec-butyl, isobutyl, —$CF_3$, —$CF_2CF_3$, =$CH_2$, =$CHCH_3$, =$CHCH_2CH_3$, =$C(CH_3)_2$, =$CHCH_2CH_2CH_3$, and =$C(CH_3)(CH_2CH_3)$;

$R_{22}$ is chosen from methyl, ethyl, propyl, butyl, —$CF_3$, and —$CF_2CF_3$; and $R_{23}$ is hydrogen or when appropriate is no substituent.

The present invention further includes insecticidal compositions comprising one or more compounds of Formula (II):

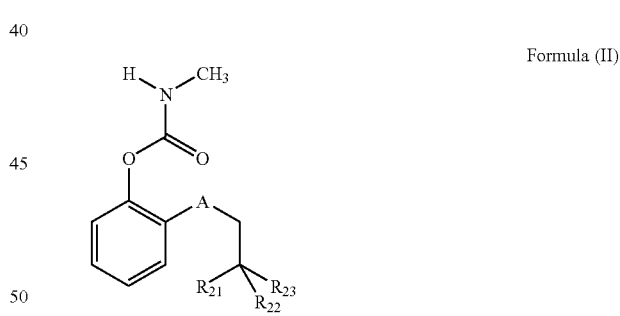

Formula (II)

wherein:

A is chosen from O and S;

$R_{21}$ is chosen from methyl, ethyl, propyl, isopropyl, butyl, sec-butyl, isobutyl, —$CF_3$, —$CF_2CF_3$, =$CH_2$, =$CHCH_3$, =$CHCH_2CH_3$, =$C(CH_3)_2$, =$CHCH_2CH_2CH_3$, and =$C(CH_3)(CH_2CH_3)$;

$R_{22}$ is chosen from methyl, ethyl, propyl, butyl, —$CF_3$, and —$CF_2CF_3$; and $R_{23}$ is hydrogen or when appropriate is no substituent.

The compounds and compositions are useful for controlling mosquitoes for example when used with a substrate, especially in close proximity to humans. One such substrate for example are nets comprising one or more compounds of Formula (II) or a composition comprising one or more compounds of Formula (II):

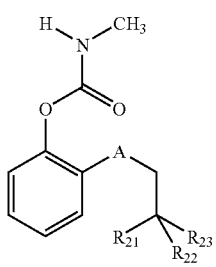

Formula (II)

wherein:

A is chosen from O and S;

R$_{21}$ is chosen from methyl, ethyl, propyl, isopropyl, butyl, sec-butyl, isobutyl, —CF$_3$, —CF$_2$CF$_3$, =CH$_2$, =CHCH$_3$, =CHCH$_2$CH$_3$, =C(CH$_3$)$_2$, =CHCH$_2$CH$_2$CH$_3$, and =C(CH$_3$)(CH$_2$CH$_3$);

R$_{22}$ is chosen from methyl, ethyl, propyl, butyl, —CF$_3$, and —CF$_2$CF$_3$; and R$_{23}$ is hydrogen or when appropriate is no substituent.

In accordance with the present invention, preferred compounds of Formula (II) include, for example, 2-(2-ethylbutylthio)phenyl-N-methylcarbamate; 2-(2-ethylbutoxy)phenyl-N-methyl carbamate; 2-(2-methylbutylthio)phenyl-N-methylcarbamate; and 2-isobutoxyphenyl-N-methyl carbamate. Compositions comprising one or more compounds of Formula (II), as well as compounds and compositions for indoor residual spraying and nets and/or other substrates comprising insecticidal carbamates include 2-(2-ethylbutylthio)phenyl-N-methylcarbamate; 2-(2-ethylbutoxy)phenyl-N-methyl carbamate; 2-(2-methylbutylthio)phenyl-N-methylcarbamate; 2-(isobutylthio)phenyl-N-methyl carbamate; 2-(2-methylallylthio)phenyl-N-methylcarbamate; and 2-isobutoxyphenyl-N-methyl carbamate. Compounds of Formula (II), wherein R$_{21}$ and/or R$_{23}$ comprise a —CF$_3$ or —CF$_2$CF$_3$ group, may be desirable for increased resistance to oxidative detoxification mechanisms in the insect thus conferring greater toxicity to mosquitoes. Exemplary compounds include, for example, 2-(3,3,3-trifluoro-2-methylpropylthio)phenyl N-methylcarbamate; 2-(2-(trifluoromethyl)butylthio)phenyl N-methylcarbamate; 2-(3,3,4,4,4-pentafluoro-2-methylbutylthio)phenyl N-methylcarbamate; 2-(3,3,4,4,4-pentafluoro-2-(trifluoromethyl)butylthio)phenyl N-methylcarbamate; 2-(2-ethyl-3,3,4,4,4-pentafluorobutylthio)phenyl N-methylcarbamate; 2-(3,3,4,4,4-pentafluoro-2-(perfluoroethyl)butylthio)phenyl N-methylcarbamate; 2-(3,3,3-trifluoro-2-methylpropoxy)phenyl N-methylcarbamate; 2-(2-(trifluoromethyl)butoxy)phenyl N-methylcarbamate; 2-(3,3,4,4,4-pentafluoro-2-methylbutoxy)phenyl N-methylcarbamate; 2-(3,3,4,4,4-pentafluoro-2-(trifluoromethyl)butoxy)phenyl N-methylcarbamate; 2-(2-ethyl-3,3,4,4,4-pentafluorobutoxy)phenyl N-methylcarbamate; 2-(3,3,4,4,4-pentafluoro-2-(perfluoroethyl)butoxy)phenyl N-methylcarbamate.

The compounds and compositions comprising one or more compounds of Formula (II) in accordance with the invention can be applied to agricultural substrates, including crops. Further applications that the compounds and compositions of the present invention are useful for include applying one or more compounds of Formula (II) or compositions comprising them in the context of indoor residual spraying or treating of nets. Specific methods of treating agricultural substrates, nets, indoor and outdoor facilities, and any other applicable substrate or use is within the capabilities of one of ordinary skill in the art and can include spraying, soaking, wiping or otherwise treating and/or applying the compounds of Formulas (I) and/or (II) or compositions comprising compounds of Formula (I) and/or (II) that may be suitable for a particular use. Compounds and compositions according to the invention can be used or formulated in accordance with routine skill in the art in light of the examples provided in this disclosure.

The methods, compositions, substrates, and nets according to the invention can comprise a synergist for increasing the lethality of a compound of Formula (II), such as for example, piperonyl butoxide.

Materials and methods relating to compounds of Formula (I). Synthesis of inhibitors: Carbamates were prepared from the corresponding phenols as described below. The phenol precursors for compounds 1a, 4a-12a were commercially available (Aldrich). The phenol precursor for compound 2a was prepared by the literature method from 3-bromophenol and Me$_3$SiCl (Wilbur, D. S.; Stone, W. E.; Anderson, K. W. Regiospecific Incorporation of Bromine and Iodine into Phenols Using (Trimethylsilyl)phenol Derivatives. *J. Org. Chem.* 1983, 48, 1542-1544); the phenol precursor for 3a was prepared similarly using EtMe$_2$SiCl, more details for which are provided in Example I. The phenol precursor for 13a was prepared by a multistep method, which is also described below. In general, synthesis of N-methyl carbamates 1a-13a was achieved by deprotonating the phenols with K(Ot-Bu) or NaH in THF, followed by the addition of N-methyl carbamoyl chloride.

Synthesis of N,N-dimethyl carbamate 1g was similarly achieved using N,N-dimethyl-carbamoyl chloride. Synthesis of N-ethyl and N-hexyl carbamates 1h and 1c was achieved using EtN(i-Pr)$_2$ as base and the corresponding isocyanates as electrophiles. Purified yields for the carbamoylation steps ranged from 60-90%. N-isopropyl carbamate 1d, N-propargyl carbamate 1e and N-(1-benzyltriazol-4-yl)methyl carbamate 1f were prepared as described below. Carbamates 1a (Kolbezen, et al., 1954); 2a (Metcalf, R. L.; Fukuto, T. R. Silicon-containing carbamate insecticides. *J. Econ. Ent.* 1965, 58, 1151 ("Metcalf 11965")); 4a-5a (Metcalf, R. L.; Fukuto, T. R. Carbamate Insecticides, Effects of Chemical Structure on Intoxication and Detoxication of Phenyl N-Methylcarbamates in Insects. *J. Agric. Food Chem.* 1965, 13, 220-231 ("Metcalf II 1965")); 6a (Kohn et al., 1965); 7a-11a (Metcalf II 1965); 1h (Kolbezen, et al., 1954); 1c (Yu, C.-C.; Kearns, C. W.; Metcalf, R. L. Acetylcholinesterase inhibition by substituted phenyl N-alkyl carbamates. *J. Agric. Food Chem.* 1972, 20, 537-540); and 1g (Metcalf, 1971) have been previously described. Detailed procedures for new compounds follow below.

EXAMPLE I

Preparation of N-methyl 3-ethyldimethylsilylphenyl carbamate (3a)

3-bromophenoxyethyldimethylsilane: To a stirred solution of 3-bromophenol (0.60 g, 3.47 mmol) in dry THF (15 mL) under nitrogen was added Et$_3$N (0.48 mL, 3.47 mmol). A clear yellow solution formed immediately; after cooling to 0° C., dimethylethylsilyl chloride (0.43 g, 0.49 mL, 3.47 mmol) was added by syringe over a period of 10 minutes. The yellow color disappeared in 10 min, and a white cloudy solution formed. After 3 hr the thick reaction mixture was filtered, washed with 15 mL of hexane, and filtered again. Concentration gave a clear oil (quantitative weight recovery) that was used in the next step without any purification.

3-ethyldimethylsilylphenol: In a 100 mL flame-dried three-necked flask, fitted with refluxing condenser and dropping funnel, magnesium (92 mg, 3.82 mmol), iodine (1 mg) and dry THF (6 mL) were placed under nitrogen. A light brown solution formed, the mixture was heated to reflux, and a solution of 3-bromophenoxydimethylsilane (0.899 g, 3.47 mmol) in THF (20 mL) was added by dropping funnel over 2 hr. The reaction mixture was refluxed overnight and cooled to room temperature. Ethyldimethylchlorosilane (0.681 g, 0.78 mL, 5.55 mmol) was then added by syringe. The reaction mixture was brought to reflux again for 6 hr, and allowed to stir overnight at room temperature. The reaction was then quenched with 1N HCl, and the reaction concentrated in vacuo. Extraction with $CH_2Cl_2$, aqueous workup, and column chromatography (n-hexane/ethyl acetate 8:1) yielded 3-ethyldimethylsilyl phenol (0.130 g, 0.73 mmol, 21%) as a colorless oil.

N-methyl 3-(ethyldimethylsilyl)phenyl carbamate: To a stirred suspension solution of sodium hydride (31 mg, 60%, 1.28 mmol) in THF (6 mL) was added 3-ethyldimethylsilylphenol (115 mg, 0.64 mmol) at room temperature. The cloudy suspension turned clear and after 30 min, N-methyl carbamoyl chloride (151 mg, 1.41 mmol) was added by syringe. A white cloudy solution formed again in 10 min. After stirring overnight, the reaction was quenched with water, concentrated in vacuo, and extracted with $CH_2Cl_2$. The organic layer was dried with sodium sulfate, concentrated and purified by column chromatography (n-hexane/ethyl acetate 10:1) to yield N-methyl 3-(ethyldimethylsilyl)phenyl carbamate (84.3 mg, 56%) as a white solid. $^1H$ NMR ($CDCl_3$, 400 MHz) δ 0.19 (s, 6H), 0.67 (d, J=8 Hz, 2H), 0.89 (t, J=8 Hz, 3H), 2.85 (d, J=4.8 Hz, 3H), 4.95 (broad, 1H), 7.09-7.39 (m, 4H); $^{13}C$ NMR ($CDCl_3$, 100 MHz) δ −3.60, 7.29, 7.35, 27.7, 122.0, 126.2, 128.7, 130.5, 141.4, 150.6, 155.3.

EXAMPLE II

Preparation of N-methyl-3-fluoro-5-trifluoromethylphenylcarbamate (12a)

An oven-dried 25 mL round bottomed flask was charged with 251 mg (1.39 mmol) 3-fluoro-5-(trifluoromethyl)phenol and purged with nitrogen. After cooling to 0° C., 1.6 mL 1 M KOt-Bu in THF (1.6 mmol) was added by syringe. After stirring for 20 min, 196 mg (2.1 mmol) N-methylcarbamoyl chloride was added by syringe and the reaction was allowed to warm to room temperature. After 18 hrs the reaction was concentrated in vacuo and the residue was taken up in $CH_2Cl_2$, washed with 0.25 M HCl, $H_2O$, and brine. The organic layer was dried ($Na_2SO_4$), filtered, and concentrated in vacuo to give a residue that was chromatographed on silica w/2.5:1 hexane:ethyl acetate to give a feathery white solid (195 mg, 59% yield). $^1H$ NMR ($CDCl_3$) δ 2.92 (s, 3H), 5.05 (s, 1H), 7.09-7.26 (m, 3H); $^{13}C$ NMR ($CDCl_3$) δ 27.82, 109.74, 113.16 (d, $J_{CF}$=24 Hz), 114.81, 123.00 (q, $J_{CF}$=275 Hz); 132.77 (dq, $J_{CF}$=34, 9.5 Hz), 152.40 (d, $J_{CF}$=10 Hz), 154.02, 162.60 (d, $J_{CF}$=248 Hz).

EXAMPLE III

Preparation of N-methyl 3-(1-benzyl-1H-1,2,3-triazol-4-yl)phenyl carbamate (13a)

3-ethynylphenol: To a stirred solution of $PdCl_2(PPh_3)_2$ (46 mg, 0.04 mmol), CuI (15 mg, 0.08 mmol), and $Et_3N$ (0.303 g, 0.42 mL, 3 mmol) in 10 mL of THF under nitrogen was added 3-iodophenol (0.440 g, 2 mmol) by syringe. The reaction mixture was cooled to 0° C., and trimethylsilylacetylene (0.206 g, 0.30 mL, 2.1 mmol) was added dropwise over 30 min. The reaction mixture was stirred at room temperature overnight and was filtered through Celite to remove Pd and Cu catalysts. Column chromatography (n-hexane/Acetone 6:1) yielded 3-(2-(trimethylsilyl)ethynyl)phenol (380 mg, 2.0 mmol, >99%) as a light brown oil. This compound was diluted with THF (6 mL) and MeOH (6 mL), and 10% aqueous KOH (6 mL) was added. After stirring for 2 hr, the reaction mixture was neutralized by 1 N HCl and evaporated, extracted with $CH_2Cl_2$, and dried ($Na_2SO_4$). Column chromatography (n-hexane/acetone 5:1) yielded 3-ethynylphenol (162.8 mg, 70%) as a yellow oil.

3-(1-benzyl-1H-1,2,3-triazol-4-yl)phenyl methylcarbamate: To a stirred solution of 3-ethynylphenol (100 mg, 0.85 mmol) and benzylazide (115 mg, 0.86 mmol) in 1:1 tert-butanol: water (3 mL) was added sodium ascorbate (16.8 mg, 0.085 mmol), followed by $CuSO_4 5H_2O$ (2.12 mg, 0.0085 mmol). (Rostovtsev, V. V.; Green, L. G.; Fokin, V. V.; Sharpless, K. B. A Stepwise Huisgen Cycloaddition Process: Copper(I)-Catalyzed Regioselective "Ligation" of Azides and Terminal Alkynes. *Angew. Chem. Int. Ed.* 2002, 41, 2596-2599.) The reaction mixture was stirred for 24 h, evaporated, extracted with $CH_2Cl_2$, and dried ($Na_2SO_4$). Column chromatography (n-hexane/ethyl acetate 2:1) yielded the desired product (120.0 mg, 0.48 mmol, 57%) as a white solid.

N-methyl-3-(1-benzyl-1H-1,2,3-triazol-4-yl)phenyl carbamate: To a stirred solution of the above triazole (120 mg, 0.48 mmol) in THF (6 mL) was added KOt-Bu (0.53 mL, 1 M, 0.53 mmol) by syringe under ice/water bath. The yellow solution formed and after 30 min, N-methyl carbamoyl chloride (89 mg, 0.96 mmol) was added. The reaction was quenched with water after stirring overnight, concentrated in vacuo, extracted with $CH_2Cl_2$ and the organic layer was dried ($Na_2SO_4$). Column chromatography (n-hexane/ethyl acetate 3:1, 1:1) yielded N-methyl 3-(1-benzyl-1H-1,2,3-triazol-4-yl)phenyl carbamate (126 mg, 0.41 mmol, 86%) as a white solid. $^1H$ NMR ($CDCl_3$, 400 MHz) δ 2.89 (d, J=4.8 Hz, 3H), 5.03 (broad, 1H), 5.57 (s, 2H), 7.08 (dd, J=1.2, 8.0 Hz, 1H), 7.29~7.40 (m, 6H), 7.55 (s, 1H), 7.65~7.66 (m, 2H); $^{13}C$ NMR ($CDCl_3$, 100 MHz) δ 27.7, 54.2, 118.9, 119.8, 121.3, 122.6, 128.1, 128.8, 129.2, 129.7, 131.9, 134.5, 147.5, 151.5.

EXAMPLE IV

Preparation of N-isopropyl-3-tert-butylphenylcarbamate (1d)

An oven-dried 5 mL round bottomed flask was charged with 224 mg (1.49 mmol) 3-t-butylphenol, and purged with nitrogen. The flask was placed in an ice-bath and 1.57 mL 1M KOt-Bu in THF (1.57 mmol) was added by syringe. After stirring for 30 min, isopropyl isocyanate (154 uL, 1.57 mmol) was added by syringe and the reaction was allowed to come to room temperature. After 2 hr a white solid mass had formed, which dissolved upon addition of 1 mL of dry THF. After a total of 24 hours, the solvent was removed in vacuo, and the residue taken up in $CH_2Cl_2$, washed with 0.25 M HCl, $H_2O$, and brine. The organic layer was dried ($Na_2SO_4$), filtered, and concentrated in vacuo to give a 218.5 mg of an oil that was pure by $^1H$ NMR spectroscopy. (62% yield). $^1H$ NMR ($CDCl_3$) δ 1.30 (s, 9H), 1.46 (d, J=7.2 Hz, 6H), 5.00 (7-let, J=7.2 Hz, 1H), 5.02 (s, 1H), 6.66 (d, J=7.6 Hz, 1H), 6.88 (s, 1H), 6.97 (d, J=7.7, 1H), 7.17 (t, J=7.7 Hz, 1H); $^{13}C$ NMR ($CDCl_3$) δ 19.65, 28.55, 31.36, 47.86, 112.35, 112.67, 117.88, 129.25, 148.79, 153.41, 155.44.

EXAMPLE V

Preparation of N-propargyl 3-t-butylphenyl Carbamate (1e)

An oven-dried 25 mL flask was charged with dry $CH_2Cl_2$ (5 mL), 3-t-butylphenol (100 mg, 0.67 mmol), bis(4-nitrophenyl) carbonate (405 mg, 1.34 mmol) and 4-DMAP (162 mg, 1.34 mmol). The reaction was stirred overnight at room temperature and then evaporated. Column chromatography (n-hexane/ethylacetate 8:1) yielded 3-t-butylphenyl 4-nitrophenyl carbonate (189 mg, 0.60 mmol, 90%). This carbonate was dissolved in dry $CH_2Cl_2$ (8 mL) and 4-DMAP (162 mg, 1.34 mmol) was added. After 15 min, propargylamine (73 mg, 0.085 ml, 1.34 mmol) was added by syringe. The reaction was allowed to stir overnight at room temperature and then evaporated. Column chromatography (n-hexane/ethylacetate 15:1) yielded N-propargyl-3-t-butylphenyl carbamate (93 mg, 0.40 mmol, 60%). $^1H$ NMR ($CDCl_3$, 400 MHz) δ 1.32 (t, 9H), 2.30 (s, 1H), 4.08 (d, J=5.2 Hz, 2H), 5.27 (broad, 1H), 6.97 (d, J=7.2 Hz, 1H), 7.13 (d, J=2.0 Hz, 1H), 7.23~7.31 (m, 2H); $^{13}C$ NMR ($CDCl_3$, 100 MHz) δ 30.9, 31.2, 34.7, 72.0, 79.3, 118.5, 122.5, 128.8, 150.6, 152.9, 154.2.

EXAMPLE VI

Preparation of N-(1-benzyl-1H-1,2,3-triazol-4-yl) methyl 3-t-butylphenyl Carbamate (1f)

To a stirred solution of N-propargyl-3-t-butylphenyl carbamate 1e (48.9 mg, 0.21 mmol) and benzylazide (31 mg, 0.23 mmol) in 1:1 t-butanol:water (2 mL) was added sodium ascorbate (4.2 mg, 0.021 mmol), followed by $CuSO_4.5H_2O$ (0.52 mg, 0.0021 mmol). The reaction mixture was stirred for 24 h, evaporated, extracted with $CH_2Cl_2$, dried, and purified by column chromatography (n-hexane/ethyl acetate 1:1) to yield the desired product (47.4 mg, 0.13 mmol, 60%). $^1H$ NMR ($CDCl_3$, 400 MHz) δ 1.29 (t, J=19.6 Hz, 9H), 4.51 (d, J=5.6 Hz, 2H), 5.51 (s, 2H), 5.69 (broad, 1H), 6.91 (d, J=7.6 Hz, 1H), 7.08 (t, J=2.0 Hz, 1H), 7.20~7.39 (m, 7H), 7.51 (s, 1H); $^{13}C$ NMR ($CDCl_3$, 100 MHz) δ 31.2, 34.7, 36.6, 54.2, 118.6, 122.2, 122.5, 128.1, 128.7, 128.8, 129.1, 134.4, 145.0, 150.7, 152.9, 154.8.

Materials and Methods Relating to Compounds of Formula (II). Synthesis of inhibitors: Synthesis of 2-substituted-phenyl methylcarbamates 1b-2b, 4b-23b was achieved by deprotonating the corresponding phenols 1p-2p, 4p-23p with KOt-Bu in THF, followed by the addition of N-methylcarbamoyl chloride. Purified yields for the carbamoylation steps ranged from 60-90%. Carbamate 3b was prepared by MCPBA oxidation of 2b. Carbamates 8c-e were prepared by reaction of 8p with ethyl isocyanate, hexylisocyanate, and N,N-dimethylcarbamoyl chloride, respectively. Phenols 1p, 4p-9p, 11p, 14p-19p bearing a 2-thioalkyl substituent were prepared by alkylation of 2-mercaptophenol as described below. Phenols 2p, 10p, 12p-13p, 20p-21p were prepared by alkylation of catechol, as described below. Phenols 22p-23p were purchased from Aldrich. Carbamates 5b (Metcalf, R. L.; Fukuto, T. R.; Frederickson, M.; Peak, L. Insecticide Screening, Insecticidal Activity of Alkylthiophenyl N-Methylcarbamates. *J. Agric. Food Chem.* 1965, 13, 473-477 ("Metcalf III 1965")); 6b (Hammann, Ingeborg; Heiss, Rudolf, Schegk, Ernst; Schrader, Gerhard; Wedemeyer, Karlfried. Termite-resistant carbamates. (1963), 3 pp. DE 1148107 19630502 CAN 59:18153 AN 1963:418153 CAPLUS); 8b (Hammann, 1963); 14b (Hammann, 1963); 16b (Metcalf III 1965 and Hammann, 1963); 19b (Mahfouz, A. M. M.; Metcalf, R. L.; Fukuto, T. R. Influence of the sulfur atom on the anticholinesterase and insecticidal properties of thioether N-methylcarbamates. *J. Agric. Food Chem.* 1969, 17, 917-922); 22b (Metcalf, R. L.; Fukuto, T. R. Effects of molecular structure upon anticholinesterase and insecticidal activity of substituted phenyl N-methylcarbamates. *J. Agric. Food Chem.* 1967, 15, 1022-1029); 23b (Kohn, G. K.; Ospenson, J. N.; Moore, J. E. Some Structural Relationships of a Group of Simple Alkyl Phenyl N-Methylcarbamates to Anticholinesterase Activity. *J. Agric. Food Chem.* 1965, 13, 232-235) have been previously described; all others are novel.

EXAMPLE VII

General procedure for S-alkylation of 2-mercaptophenol with activated (allylic) halides. 16p: 2-(allylthio)phenol. An oven-dried 10 mL round-bottom flask was equipped with a magnetic stir bar and septum, purged with nitrogen, and charged with 1 M KOt-Bu in THF (3.49 mL, 3.49 mmol) and cooled to 0° C. Addition of 2-mercaptophenol (400 mg, 3.17 mmol) via syringe resulted in a yellow precipitate that was allowed stir for 20 minutes prior to the dropwise addition of allyl bromide (460 mg, 3.80 mmol), which caused dissolution of the yellow precipitate and formation of a white suspension. The ice bath was removed, and after stirring for 18 h, the solvent was removed in vacuo, and the residue was dissolved in dichloromethane (10 mL). The solution was washed with 0.25 M HCl (1×5 mL), and saturated NaCl (1×5 mL). The combined aqueous layers were extracted with dichloromethane (2×5 mL), and the combined organic extracts were dried with sodium sulfate, filtered, and concentrated in vacuo. Purification was performed by flash chromatography on silica gel w/6:1 hexane:ethyl acetate to give a colorless oil weighing 454 mg (86% yield). $^1H$ NMR ($CDCl_3$): δ 3.30 (d, J=6.60 Hz, 2H), 4.86-4.90 (m, 1H), 4.99-5.01 (m, 1H), 5.77-5.86 (m, 1H), 6.70 (s, 1H), 7.87 (dt, J=1.40 Hz, J=7.45 Hz, 1H), 6.99 (dd, J=1.40 Hz, J=7.95 Hz, 1H), 7.27 (dt, J=1.65 Hz, J=7.45 Hz, 1H), 7.44 (dd, J=1.65 Hz, J=7.70 Hz); $^{13}C$ NMR ($CDCl_3$): δ 39.92, 114.83, 118.18, 118.33, 120.72, 131.38, 133.20, 136.54, 157.25; HRMS (FAB): 166.04524 calcd for $C_9H_{10}OS$ $[M]^+$ found 166.04633 (6.4 ppm, 1.1 mmu).

General procedure for the preparation of N-methylcarbamoylation of phenols. 16b: 2-(allylthio)phenyl-N-methylcarbamate. An oven-dried 5 mL round-bottom was charged with 2-(allylthio)phenol 16p (152 mg, 0.914 mmol) and a magnetic stir bar, sealed with a septum, purged with $N_2$, and cooled to 0° C.; 1.0 mL 1M KOt-Bu in THF (1.0 mmol) was then added via syringe. After stirring for 30 min, N-methylcarbamoyl chloride 133 mg (1.4 mmol) was added as a solution in 1 mL THF; after 15 min the ice bath was removed and the reaction was allowed to stir at room temperature for 24 h. Workup was performed by removal of solvent in vacuo, addition of dichloromethane (10 mL) and 0.25 M HCl (5 mL). The organic layer was removed and the aqueous layer extracted twice with 5 mL dichloromethane. The combined organic extracts were dried over sodium sulfate, filtered, and concentrated in vacuo. Purification was carried out by flash chromatography on silica gel (2:1 hexane:ethyl acetate) to afford a pale yellow oil that crystallized into an off-white solid weighing 179 mg (0.802 mmol) 88% yield. 1H NMR ($CDCl_3$): δ 2.91 (d, J=4.95 Hz, 3H), 3.51 (d, J=6.60 Hz, 2H), 5.05 (s, 1H), 5.07 (dd, J=1.5 Hz, J=10 Hz, 1H), 5.15 (dq, J=1.5 Hz, J=17 Hz, 1H), 5.83-5.88 (m, 1H), 7.12-7.21 (m, 3H), 7.34 (dd, J=1.5 Hz, J=7.5 Hz); $^{13}C$ NMR ($CDCl_3$): δ 27.96, 36.32, 118.14, 123.04, 126.06, 127.40, 129.36, 130.78, 133.32, 149.68, 154.75; HRMS (FAB): 224.0745 calcd for $C_{11}H_{13}NO_2S$ $[M+H]^+$ found 224.0748 (1.2 ppm, 0.3 mmu).

EXAMPLE VIII

General procedure for the S-alkylation of 2-mercaptophenol with saturated alkyl halides. 1p: 2-(2-ethylbutylthio)phenol. An oven-dried 50 mL round-bottom flask was charged with 2-mercaptophenol (1.00 g, 7.56 mmols), DMF (dried, 8.0 mL) and sodium bicarbonate (950 mg, 11.3 mmol) while purging with nitrogen. 1-Bromo-2-ethylbutane (2.25 g, 13.6 mmol) was added and the reaction was stirred at 55° C. for 18 hours. The reaction was cooled, diluted with 1:1 sat'd NaCl: 1M HCl (80 mL) extracted with EtOAc (3×50 mL). The organic layers were combined, dried over sodium sulfate, filtered, and concentrated in vacuo. The residue was purified by flash chromatography (4:1 hexane:ethyl acetate), affording a pale oil weighing 1.314 g (83% yield). $^1H$ NMR ($CDCl_3$): δ 0.84 (t, J=4.77 Hz, 6H), 1.38-1.48 (m, 5H), 2.69 (d, J=6.70 Hz, 2H), 6.74 (s, 1H), 6.86 (dt, J=1.35, J=7.70 Hz, 1H), 6.97 (dd, J=1.40 Hz, J=8.25 Hz, 1H), 7.24 (dt, J=1.65 Hz, J=7.45 Hz, 1H), 7.46 (dd, J=1.65 Hz, J=7.70 Hz, 1H); 13C NMR ($CDCl_3$): δ 10.79, 24.92, 40.78, 41.32, 114.74, 120.06, 120.82, 130.84, 135.75, 156.79; HRMS (FAB): 210.10784 calcd for $C_{12}H_{18}OS$ $[M]^+$ found 210.10693 (-4.4 ppm, -0.9 mmu).

1b: 2-(2-ethylbutylthio)phenyl-N-methylcarbamate. Pale oil; 85% yield; $^1H$ NMR ($CDCl_3$): δ 0.87 (t, J=7.45 Hz, 6H), 1.38-1.54 (m, 6H), 2.84 (d, J=6.05 Hz, 2H), 2.90 (d, J=4.7 Hz, 3H), 5.07 (s, 1H), 7.10-7.19 (m, 3H), 7.32-7.34 (m, 1H); $^{13}C$ NMR ($CDCl_3$): δ 10.83, 25.20, 27.93, 36.92, 40.34, 122.98, 126.14, 126.56, 129.44, 131.03, 149.25, 154.79; HRMS (FAB): 268.13713 calcd for $C_{14}H_{21}NO_2S$ $[M+H]^+$ found 268.1370 (-0.5 ppm, -0.1 mmu).

EXAMPLE IX

General Procedure for O-alkylation of catechols. 2p: 2-(2-ethylbutoxy)phenol. A flame-dried 250 mL round-bottom flask was charged with catechol (4.99 g, 45.3 mmol), DMF (45 mL) and $Cs_2CO_3$ (14.7 g, 45.1 mmol) and purged with nitrogen. 2-Ethyl-1-bromobutane (5.90 g, 35.7 mmol) was added and the reaction was heated at 80° C. for 18 hours. After cooling to room temperature the reaction was diluted in 250 mL 1:1 M HCl:sat'd brine and extracted with EtOAc (3×50 mL). The combined organic layers were washed with saturated NaCl (1×25 mL), dried over sodium sulfate, and concentrated in vacuo. Purification by flash:chromatography (5:1 hexane:Ethyl acetate) afforded a colorless oil weighing 4.25 g (61% yield). $^1H$ NMR ($CDCl_3$): δ 0.94 (t, J=7.42 Hz 6H), 1.45-1.51 (m, 4H), 1.71 (s-7, J=5.71 1H), 6.81-6.88 (m, 3H), 6.92-6.94 (m, 1H); $^{13}C$ NMR ($CDCl_3$): δ 11.29, 23.59, 41.03, 70.99, 111.64, 114.52, 120.23, 121.38, 145.96, 146.26.

2b: 2-(2-ethylbutoxy)phenyl-N-methylcarbamate. White solid; 83% yield; $^1H$ NMR ($CDCl_3$): δ 0.92 (t, J=7.70 Hz, 6H), 1.38-1.52 (m, 4H), 1.64 (s-7, J=6.35 Hz, 1H), 2.88 (d, J=4.95 Hz, 3H), 3.87 (d, J=5.80 Hz, 2H), 6.89 (t, J=7.70 Hz, 1H), 6.94 (d, J=7.95 Hz, 1H), 7.07 (t, J=7.15 Hz, 1H); $^{13}C$ NMR ($CDCl_3$): δ 11.29, 23.46, 27.84, 41.11, 70.68, 113.32, 120.51, 123.17, 126.43, 140.51, 151.52, 155.13.

EXAMPLE X

3b: 2-(2-ethylbutylsulfinyl)phenyl-N-methylcarbamate. A dry 25 mL round-bottom flask was charged with carbamate 2b (72 mg, 0.269 mmol) and dichloromethane (10 mL). The solution was cooled to 0° C. before the addition of m-chloroperbenzoic acid (77 wt %, 67 mg, 0.299 mmol) in one portion. The solution was allowed to warm to room temperature and stir for 18 hours. Upon completion, the reaction was diluted in 10 mL of DCM and washed with 10% $NaHCO_3$ (2×5 mL). The organic layer was stripped and purified by flash chromatography (3:1 EtOAc:hexane) to afford a colorless oil weighing 53 mg (70% yield). $^1H$ NMR ($CDCl_3$): δ 0.86 (t, J=7.45 Hz, 3H), 0.90 (t, J=7.45 Hz, 3H), 1.31-1.40 (m, 1H), 1.43-1.54 (m, 2H), 1.62-1.71 (m, 1H), 1.92-2.00 (m, 1H), 2.73 (dd, J=5.00 Hz, J=13.4 Hz, 1H), 2.75 (dd, J=9.0 Hz, J=13.4 Hz, 1H), 2.88 (d, J=4.95 Hz, 3H), 5.37 (s, 1H), 7.16 (dd, J=1.35 Hz, J=7.95 Hz, 1H), 7.40-7.47 (m, 2H), 7.89 (dd, J=1.65 Hz, J=7.45 Hz, 1H); $^{13}C$ NMR ($CDCl_3$): δ 10.08, 10.80, 24.65, 25.71, 27.98, 35.96, 61.71, 122.73, 125.10, 126.70, 131.85, 137.33, 146.77, 154.12; HRMS (FAB): 284.13204 calcd for $C_{14}H_{21}NO_3S$ $[M+1]^+$ found 284.13196 (−0.2 ppm, −0.1 mmu).

EXAMPLE XI

4p: 2-(2-methylbutylthio)phenol. This compound was prepared in 57% yield from 2-mercaptophenol and 1-chloro-2-methylbutane according to the procedure for 1p in Example VIII. 1H NMR ($CDCl_3$): δ 0.86 (t, J=4.85 Hz, 3H), 1.00 (d, J=6.60 Hz, 3H), 1.18-1.27 (m, 1H), 1.46-1.58 (m, 2H), 2.55 (dd, J=7.15, J=12.35, 1H), 2.70 (dd, J=5.75, 12.65, 1H), 6.75 (d, J=1.1 Hz), 6.86 (dt, J=1.1 Hz, J=4.93 Hz, 1H), 6.98 (dd, J=1.4 Hz, J=8.25 Hz, 1H), 7.24 (dt, J=1.65 Hz, J=7.40 Hz, 1H), 7.45 (dd, J=1.65 Hz, J=7.70 Hz, 1H); 13C NMR ($CDCl_3$): δ 11.26, 18.74, 28.56, 34.80, 44.36, 114.77, 119.98, 120.81, 130.89, 135.80, 156.80; HRMS (FAB): 196.09219 calcd for $C_{11}H_{16}OS$ $[M]^+$ found 196.09293 (3.6 ppm, 0.7 mmu).

4b: 2-(2-methylbutylthio)phenyl-N-methylcarbamate. Pale oil; 88% yield; 1H NMR ($CDCl_3$): δ 0.89 (t, J=7.45 Hz, 3H), 1.01 (d, J=6.90 Hz, 3H), 1.21-1.30 (m, 1H), 1.49-1.58 (m, 1H), 1.60-1.68 (m, 1H), 2.69, (dd, J=7.70 Hz, J=12.4 Hz, 1H), 2.88 (dd, J=6.05 Hz, J=12.35 Hz, 1H), 2.90 (d, J=4.70 Hz, 3H), 5.08 (s, 1H), 7.09-7.19 (m, 3H), 7.30-7.32 (m, 1H); 13C NMR ($CDCl_3$): δ 11.32, 19.04, 27.93, 28.51, 28.91, 34.50, 40.01, 123.01, 126.14, 126.58, 129.42, 130.92, 149.23, 154.79; HRMS (FAB): 254.12148 calcd for $C_{13}H_{19}NO_2S$ $[M]^+$ found 254.12044 (−4.2 ppm, −1.1 mmu).

EXAMPLE XII

5p: 2-(isopropylthio)phenol. This compound was prepared in 51% yield from 2-mercaptophenol and isopropyl iodide according to the procedure for 1p in Example VIII. Colorless Oil; 1H NMR ($CDCl_3$): δ 1.25 (d, J=6.85 Hz, 6H), 3.09 (s-7, J=6.66 Hz, 1H), 6.85 (s, 1H), 6.87 (dd, J=0.10 Hz, J=7.45 Hz, 1H), 6.99 (dd, J=0.10 Hz, J=7.95 Hz, 1H), 7.27 (dd, J=1.65 Hz, J=7.95 Hz, 1H), 7.44 (dd, J=1.65 Hz, J=7.70 Hz, 1H); 13C NMR ($CDCl_3$): δ 23.36, 40.66, 114.71, 118.02, 120.61, 131.44, 137.00, 157.56; HRMS (FAB): 169.06872 calcd for $C_9H_{12}OS$ $[M+1]^+$ found 169.06956 (3.1 ppm, 0.5 mmu).

5b: 2-(isopropylthio)phenyl-N-methylcarbamate. White solid; 92% yield; 1H NMR ($CDCl_3$): δ 1.28 (d, J=6.85 Hz, 6H), 2.90 (d, J=4.95 Hz, 3H), 3.37 (s-7, J=6.60 Hz, 1H), 7.12-7.17 (m, 2H), 7.23 (t, 7.70 Hz, 1H), 7.41 (d, J=7.70 Hz, 1H); $^{13}C$ NMR ($CDCl_3$): δ 23.29, 27.98, 37.50, 123.24, 126.05, 127.87, 129.14, 132.73, 150.57, 154.89; HRMS (FAB): 226.09018 calcd for $C_{11}H_{15}NO_2S$ $[M+1]^+$ found 226.0896 (−2.5 ppm, −0.6 mmu).

EXAMPLE XIII

6b: 2-(isobutylthio)phenyl-N-methylcarbamate. Brown Oil; 90% yield; 1H NMR ($CDCl_3$): δ 1.02 (d, J=6.60 Hz, 6H), 1.85 (septet, J=6.90 Hz, 1H), 2.75 (d, J=6.85 Hz, 2H), 2.91 (d, J=4.95 Hz, 3H), 5.06 (s, 1H), 7.10-7.19 (m, 3H), 7.30-7.32 (m, 1H); 13C NMR ($CDCl_3$): δ 22.17, 27.94, 28.29, 41.87, 123.03, 126.14, 126.63, 129.51, 130.79, 149.25, 154.78; HRMS (FAB): 240.10583 calcd for $C_{12}H_{17}NO_2S$ $[M+H]^+$ found 240.10570 (−0.5 ppm, −0.1 mmu).

EXAMPLE XIV

7p: 2-(neopentylthio)phenol. This compound was prepared in 58% yield from 2-mercaptophenol and neopentyl iodide according to the procedure for 1p in Example VIII. 1H NMR ($CDCl_3$): δ 1.03 (s, 9H), 2.70 (s, 2H), 6.72 (s, 1H), 6.83-6.87 (m, 1H), 6.96 (dd, J=2.2 Hz, J=7.95 Hz, 1H), 7.21-7.26 (m, 1H), 7.46-7.48 (m, 1H); 13C NMR ($CDCl_3$): δ 28.90, 32.56, 52.64, 114.82, 120.94, 130.74, 135.61, 156.60, 158.89;

7b: 2-(neopentylthio)phenyl-N-methylcarbamate. Yellow Oil; 94% yield; 1H NMR ($CDCl_3$): δ 1.03 (s, 9H), 2.82 (s, 2H), 2.90 (d, J=4.95 Hz, 3H), 5.09 (s, 1H), 7.09-7.18 (m, 3H), 7.35-7.37 (m, 1H); 13C NMR ($CDCl_3$): δ 27.93, 29.13, 32.35, 47.89, 122.98, 126.12, 126.65, 129.91, 131.56, 149.36, 154.83; HRMS (FAB): 254.12148 calcd for $C_{13}H_{19}NO_2S$ $[M+H]^+$ found 254.12180 (1.3 ppm, 0.3 mmu).

EXAMPLE XV

8p: 2-(2-methylallylthio)phenol. This compound was prepared in 65% yield from 2-mercaptophenol and methallyl chloride according to the procedure for 16b in Example VII. Brown Oil; 1H NMR ($CDCl_3$): δ 1.86 (s, 3H), 3.26 (s, 2H), 4.52 (s, 1H), 4.73 (s, 1H), 6.68 (s, 1H), 6.85 (dt, J=1.35 Hz, J=7.40 Hz, 1H), 6.97 (dd, J=1.1, J=8.0 Hz, 1H), 7.25 (dt, J=1.4, J=7.7, 1H), 7.39 (dd, J=1.7 Hz, J=7.7 Hz, 1H); 13C NMR ($CDCl_3$): δ 20.91, 44.49, 114.74, 114.92, 118.84, 120.67, 131.25, 136.31, 140.32, 157.08.

8b: 2-(2-methylallylthio)phenyl-N-methylcarbamate. Yellow oil; 82% yield; 1H NMR ($CDCl_3$): δ 1.83 (s, 3H), 2.89 (d, J=19.25 Hz, 3H), 3.47 (s, 2H), 4.82 (d, J=11.25 Hz, 2H), 5.04 (s, 1H), 7.22-7.11 (m, 3H), 7.34 (d, J=7.7 Hz, 1H); 13C NMR ($CDCl_3$): δ 21.31, 27.95, 41.03, 56.54, 114.35, 122.98, 126.02, 127.43, 131.15, 140.60, 149.80, 154.77; HRMS (FAB): 237.08235 calcd for $C_{12}H_{15}NO_2S$ $[M]^+$ found 237.08333 (4.0 ppm, 0.9 mmu).

EXAMPLE XVI

9p: 2-(cyclohexylmethylthio)phenol. This compound was prepared in 87% yield from 2-mercaptophenol and cyclohexylmethyl bromide according to the procedure for 1p in Example VIII. Colorless oil; 1H NMR ($CDCl_3$): 0.91-0.99, 1.10-1.24 (m, 3H), 1.39-1.47 (m, 1H), 1.62-1.67 (m, 2H), 1.85-1.87 (m, 2H), 6.74 (s, 1H), 6.85 (dt, J=1.35 Hz, J=7.70 Hz, 1H), 6.97 (dd, J=1.35 Hz, J=8.25 Hz, 1H), 7.24 (dt, J=1.65 Hz, J=7.42 Hz), 7.45 (dd, J=1.65 Hz, J=7.70 Hz); 13C NMR (CDCl$_3$): δ 26.09, 26.45, 32.70, 37.86, 44.71, 114.83, 120.20, 120.85, 130.92, 135.86, 156.88; HRMS (FAB): 222.10784 calcd for C$_{13}$H$_{18}$OS [M]$^+$ found 222.1064 (−6.5 ppm, −1.4 mmu).

9b: 2-(cyclohexylmethylthio)phenyl-N-methylcarbamate. Off-white solid; 57% yield; 1H NMR (CDCl$_3$): δ 0.99 (dq, J=2.75 Hz, J=12.35 Hz, 2H), 1.11-1.27 (m, 3H), 1.50-1.58 (m, 1H), 1.63-1.66 (m, 1H), 1.70-1.73 (m, 2H), 1.89 (d, J=13.20 Hz, 2H), 2.76 (d, J=6.90 Hz, 2H), 2.91 (d, J=4.90 Hz, 3H), 7.10-7.12 (m, 1H), 7.15-7.19 (m, 2H), 7.30-7.31 (m, 1H); 13C NMR (CDCl$_3$): δ 26.10, 26.41, 27.91, 32.94, 37.50, 40.27, 122.98, 126.11, 126.47, 129.29, 131.05, 149.17, 154.75; HRMS (FAB): 279.12930 calcd for C$_{15}$H$_{21}$NO$_2$S [M]$^+$ found 279.12891 (−1.4 ppm, −0.4 mmu).

EXAMPLE XVII

10p: 2-(cyclohexylmethoxy)phenol. An oven-dried 10 mL round-bottom flask equipped with condenser was charged with catechol (198 mg, 1.80 mmol), MeOH (2 mL), and NaOMe (102 mg, 1.89 mmol) and purged with nitrogen. (Bromomethyl)cyclohexane (319 mg, 1.80 mmol) was added and the reaction was heated to reflux for 48 hours. After cooling to room temperature the reaction was diluted with 50 mL 1M HCl and extracted with DCM (3×25 mL). The combined organic layers were washed with saturated NaCl (1×25 mL), dried over sodium sulfate, and concentrated in vacuo. Purification by flash chromatography (3:1 hexane:Ethyl acetate) afforded an off-white solid weighing 114 mg (31% yield). Off-white solid; 1H NMR (CDCl$_3$): δ 1.03-1.11 (m, 2H), 1.18-1.35 (m, 3H), 1.71-1.88 (m, 6H), 3.84 (d, J=6.35 Hz, 2H), 5.64 (s, 1H), 6.80-6.88 (m, 3H), 6.92-6.94 (m, 1H); 13C NMR (CDCl$_3$): δ 25.88, 26.59, 30.05, 37.80, 74.39, 111.77, 114.55, 120.20, 121.14, 121.38, 145.99; HRMS (FAB): 206.13068 calcd for C$_{13}$H$_{18}$O$_2$ [M]$^+$ found 206.12952 (−5.7 ppm, −1.2 mmu).

10b: 2-(cyclohexylmethoxy)phenyl-N-methylcarbamate. White solid; 45% yield; 1H NMR (CDCl$_3$): δ 1.03-1.10 (m, 2H), 1.14-1.22 (m, 1H), 1.28 (dt, J=3.30 Hz, J=12.65 Hz, 2H), 1.68-1.86 (m, 6H), 2.89 (d, J=4.95 Hz, 3H), 3.78 (d, 6.05 Hz, 2H), 4.99 (s, 1H), 6.88-6.93 (m, 2H), 7.07 (d, J=7.95 Hz, 1H), 7.13 (t, J=7.45 Hz, 1H); 13C NMR (CDCl$_3$): δ 25.94, 26.63, 27.86, 29.78, 37.84, 74.09, 113.54, 120.56, 123.14, 126.39, 140.53, 151.46, 155.15.

EXAMPLE XVIII

11p: 2-(cyclopentylmethylthio)phenol. This compound was prepared in 83% yield from 2-mercaptophenol and cyclopentylmethyl tosylate according to the procedure for 1p in Example VIII. Colorless oil; 1H NMR (CDCl$_3$): δ 1.20-1.26 (m, 2H), 1.50-1.65 (m, 4H), 1.78-1.84 (m, 2H), 1.99 (s-7, J=7.45 Hz, 1H), 2.68 (d, J=7.40 Hz, 2H), 6.78 (s, 1H), 6.85 (dt, J=1.35 Hz, J=7.55 Hz, 1H), 7.24 (dt, J=1.65 Hz, J=7.85 Hz, 1H), 7.46 (dd, J=1.65, J=7.70 Hz, 1H); 13C NMR (CDCl$_3$): δ 25.38, 32.32, 39.71, 43.33, 114.74, 119.64, 120.79, 130.94, 135.89, 156.90; HRMS (FAB): 208.09219 calcd for C$_{12}$H$_{16}$OS [M]$^+$ found 208.09134 (−4.3 ppm, −0.9 mmu).

11b: 2-(cyclopentylmethylthio)phenyl-N-methylcarbamate. White solid; 78% yield; 1H NMR (CDCl$_3$): δ 1.25-1.32 (m, 2H), 1.50-1.58 (m, 2H), 1.60-1.67 (m, 2H), 1.82-1.88 (m, 2H), 2.10 (s-7, J=7.70 Hz, 1H), 2.87 (d, J=7.15 Hz, 2H), 2.90 (d, J=4.95 Hz, 3H), 5.09 (s, 1H), 7.10-7.12 (m, 1H), 7.14-7.19 (m, 2H), 7.32-7.34 (m, 1H); 13C NMR (CDCl$_3$): δ 25.30, 27.93, 28.51, 32.53, 39.12, 39.35, 122.99, 126.10, 126.58, 129.42, 130.86, 149.17, 154.78.

EXAMPLE XIX

12p: 2-(cyclopentylmethoxy)phenol. This compound was prepared in 44% yield from catechol and cyclopentylmethyl tosylate according to the general procedure for 2p in Example IX, except that potassium carbonate was used in place of cesium carbonate. Yellow oil; 1H NMR (CDCl$_3$): δ 1.33 (m, 2H), 1.58-1.69 (m, 4H), 1.82-1.89 (m, 2H), 2.40 (s-7, J=7.70 Hz, 1H), 3.91 (d, J=7.15 Hz, 2H), 5.66 (s, 1H), 6.81-6.88 (m, 3H), 6.92-6.94 (m, 1H); 13C NMR (CDCl$_3$): δ 25.53, 29.54, 39.11, 73.20, 111.78, 114.49, 120.16, 121.40, 145.90, 146.16.

12b: 2-(cyclopentylmethoxy)phenyl-N-methylcarbamate. White solid; 85% yield; 1H NMR (CDCl$_3$): δ 1.35-1.41 (m, 2H), 1.53-1.66 (m, 4H), 1.75-1.83 (m, 2H), 2.35 (s-7, J=7.40 Hz, 1H), 2.89 (d, J=4.95 Hz, 3H), 3.86 (d, J=6.60 Hz, 2H), 6.90 (t, J=7.65 Hz, 1H), 6.94 (d, J=8.25 Hz, 1H), 7.08 (d, J=7.95 Hz, 1H), 7.14 (t, J=7.40 Hz, 1H); 13C NMR (CDCl$_3$): δ 25.65, 27.88, 29.33, 39.12, 72.83, 113.59, 120.62, 123.18, 126.42, 140.49, 151.48, 155.15.

EXAMPLE XX

13p: 2-isobutoxyphenol. A 50 mL round-bottom flask was charged with catechol (499 mg, 4.53 mmol), CH$_3$CN (4.5 mL), and Cs$_2$CO$_3$ (1.50 g, 4.60 mmol) and purged with nitrogen. This white suspension was allowed to stir for 10 minutes prior to the addition of 1-iodo-2-methylpropane (1.67 g, 9.06 mmol). The reaction was brought to reflux and allowed to stir for 18 h. After cooling to room temperature the solvent was concentrated in vacuo, and the residue partitioned between ethyl acetate (50 mL) and 1 N HCl (50 mL). The organic layer was separated, dried, filtered, and concentrated in vacuo. Flash chromatography (3:1 hexane:ethyl acetate) afforded a yellow oil weighing 316 mg (30% yield). 1H NMR (CDCl$_3$): δ 1.05 (dd, J=1.95 Hz, J=6.85 Hz, 6H), 2.13 (s-7, J=6.60 Hz), 3.81 (d, J=6.60 Hz), 6.81-6.88 (m, 3H), 6.93-6.95 (m, 1H); 13C NMR (CDCl$_3$): δ 19.39, 28.38, 75.31, 111.77, 114.57, 120.22, 121.12, 121.44, 146.16.

13b: 2-isobutoxyphenyl-N-methylcarbamate. White solid; 90% yield; 1H NMR (CDCl$_3$): δ 1.01 (d, J=6.85 Hz, 6H), 2.08 (s-7, J=6.85 Hz, 1H), 2.88 (d, J=4.95 Hz, 3H), 3.75 (d, J=6.30 Hz, 2H), 5.01 (s, 1H), 6.89-6.94 (m, 2H), 7.08 (d, J=7.95 Hz, 1H), 7.14 (t, J=7.40 Hz, 1H); 13C NMR (CDCl$_3$): δ 19.23, 27.92, 28.47, 75.02, 113.53, 120.65, 123.24, 126.47, 140.52, 151.47, 155.22.

EXAMPLE XXI

14p: 2-(2-chloroallylthio)phenol. This compound was synthesized in 49% yield from 2-mercaptophenol and 2-chloroallyl chloride according to the general procedure for 16p in Example VII. Pale oil; 1H NMR (CDCl$_3$): 3.48 (d, J=0.7 Hz, 2H), 4.91 (d, J=0.65 Hz, 1H), 5.13 (d, J=1.35 Hz, 1H), 6.69 (s, 1H), 6.87 (dt, J=1.40 Hz, J=7.42 Hz, 1H), 6.99 (dd, J=1.35, J=8.25 Hz, 1H), 7.27 (dt, J=1.65 Hz, J=7.82 Hz, 1H), 7.45 (dd, J=1.65 Hz, J=7.70 Hz, 1H); 13C NMR (CDCl$_3$): 45.30, 115.08, 115.98, 117.31, 120.91, 131.89, 136.59, 137.25, 157.56; HRMS (FAB): 200.00626 calcd for C$_9$H$_9$ClOS [M]$^+$ found 200.00598 (−1.3 ppm, −0.3 mmu).

14b: 2-(2-chloroallylthio)phenyl-N-methylcarbamate. Pale Oil; 58% yield; 1H NMR (CDCl$_3$): δ 2.92 (d, J=4.65, 3H), 3.66 (s, 2H), 5.09 (s, 1H), 5.22 (d, J=15.15 Hz, 2H), 7.15-7.40 (m, 3H), 7.41 (d, J=7.70 Hz, 1H); 13C NMR (CDCl$_3$): δ 27.97, 42.04, 115.24, 123.23, 126.21, 127.70, 128.76, 132.90, 137.51, 141.99, 150.69; HRMS (FAB): 258.03556 calcd for C$_{11}$H$_{12}$NO$_2$SCl [M+H]$^+$ found 258.03574 (0.6 ppm, 0.2 mmu).

EXAMPLE XXII

15p: 2-(2-bromoallylthio)phenol. This compound was prepared from 2-mercaptophenol and 2-bromoallyl bromide in 58% yield according to the general procedure given for 16p in Example VII. Yellow oil; 1H NMR (CDCl$_3$): δ 3.57 (s, 2H), 5.33 (d, J=14.55 Hz, 2H), 6.69 (d, J=2.50 Hz, 1H), 6.87, (t, J=7.40 Hz, 1H), 6.99 (d, J=8.25 Hz, 1H), 7.28 (t, J=7.70 Hz, 1H), 7.45 (d, J=7.70 Hz, 1H); 13C NMR (CDCl$_3$): δ 47.63, 115.12, 120.39, 120.93, 124.92, 128.39, 131.89, 136.60, 157.56; HRMS (FAB): 243. 9557 calcd for C$_9$H$_9$BrOS [M]$^+$ found 243.9557.

15b: 2-(2-bromoallylthio)phenyl-N-methylcarbamate. Yellow Oil; 35% yield; 1H NMR (CDCl$_3$): δ 2.92 (d, J=4.95 Hz, 3H), 3.76 (s, 2H), 5.09 (s, 1H), 5.44 (s, 1H), 5.69 (s, 1H), 7.15-7.29 (m, 3H), 7.40 (dd, J=1.40 Hz, J=7.70 Hz); 13C NMR (CDCl$_3$): δ 27.98, 44.04, 119.61, 123.23, 126.24, 126.31, 128.38, 128.68, 132.67, 150.55, 154.80.

EXAMPLE XXIII

17p: (E)-2-(but-2-enylthio)phenol. This compound was prepared from 2-mercaptophenol and (E)-2-butenyl bromide in 97% yield according to the general procedure for 16p in Example VII. Colorless oil; 1H NMR (CDCl$_3$): δ 1.61 (d, J=0.8 Hz, 3H), 3.26 (d, J=7.40 Hz, 2H), 5.26-5.33 (m, 1H), 5.43-5.50 (m, 1H), 6.73 (s, 1H), 6.87 (dt, J=1.35 Hz, J=7.40 Hz, 1H), 6.99 (dd, J=1.10 Hz, 8.25 Hz, 1H), 7.27 (dt, J=1.65 Hz, J=7.40 Hz, 1H), 7.43 (dd, J=1.65 Hz, J=7.70 Hz, 1H); 13C NMR (CDCl$_3$): δ 17.79, 39.40, 114.69, 118.57, 120.59, 125.77, 128.88, 131.27, 136.65, 157.28.

17b: (E)-2-(but-2-enylthio)phenyl-N-methylcarbamate Colorless oil; 91% yield; 1H NMR (CDCl$_3$): δ 1.66 (d, J=6.05 Hz, 3H), 2.92 (d, J=5.00 Hz, 3H), 3.49 (d, J=6.90 Hz, 2H), 5.08 (s, 1H), 5.50-5.55 (m, 1H), 5.63-5.59 (m, 1H), 7.13-7.23 (m, 3H), 7.34 (dd, J=2.00 Hz, J=8.00 Hz, 1H); 13C NMR (CDCl$_3$): δ 17.85, 27.94, 35.49, 122.98, 125.73, 126.01, 127.09, 129.60, 130.39, 149.43, 154.79; HRMS (FAB): 238.09018 calcd for C$_{12}$H$_{15}$NO$_2$S [M+H]$^+$ found 238.08942 (−3.3 ppm, −0.8 mmu).

EXAMPLE XXIV

18p: 2-(3-methylbut-2-enylthio)phenol. This compound was prepared in 99% yield from 2-mercaptophenol and 3-methyl-2-butenylbromide according to the general procedure for 16p in Example VII. Colorless Oil; 1H NMR (CDCl$_3$): δ 1.29 (s, 3H), 1.66 (s, 3H), 3.30 (d, J=8.00 Hz, 2H), 5.21-5.26 (m, 1H), 6.82 (s, 1H), 6.84 (dt, J=1.35 Hz, J=7.40 Hz, 1H), 6.96 (dd, J=1.10 Hz, J=8.25 Hz, 1H), 7.26 (dt, J=1.65 Hz, J=7.70 Hz, 1H), 7.43 (dd, J=1.95 Hz, J=7.70 Hz, 1H); 13C NMR (CDCl$_3$): δ 17.25, 25.70, 34.79, 114.56, 118.66, 119.14, 120.53, 131.31, 136.87, 137.25, 157.44; HRMS (FAB): 194.07654 calcd for C$_{11}$H$_{14}$OS [M]$^+$ 194.0771 (2.9 ppm, 0.6 mmu).

18b: 2-(3-methylbut-2-enylthio)phenyl-N-methylcarbamate. White crystalline solid; 80% yield; 1H NMR (CDCl$_3$): δ 1.66 (d, J=6.05 Hz, 3H), 2.92 (d, J=5.00 Hz, 3H), 3.49 (d, J=6.90 Hz, 2H), 5.08 (s, 1H), 5.50-5.55 (m, 1H), 5.63-5.59 (m, 1H), 7.13-7.23 (m, 3H), 7.34 (dd, J=2.00 Hz, J=8.00 Hz, 1H); 13C NMR (CDCl$_3$): δ 17.77, 25.77, 27.94, 31.44, 118.87, 122.95, 126.03, 127.05, 130.35, 130.48, 137.12, 149.46, 154.80; HRMS (FAB): 251.09800 calcd for C$_{13}$H$_{17}$NO$_2$S [M]$^+$ found 251.0963 (−6.8 ppm, −1.7 mmu).

EXAMPLE XXV

19p: 2-(benzylthio)phenol. This compound was prepared in 78% yield from 2-mercaptophenol and benzyl bromide according to the procedure for 16p in Example VII. Pale Oil; 1H NMR (CDCl$_3$): δ 3.87 (s, 2H), 6.56 (s, 1H), 6.83 (t, J=7.30 Hz, 1H), 6.95 (d, J=8.00 Hz, 1H), 7.10 (m, 2H), 7.26-7.29 (m, 5H); 13C NMR (CDCl$_3$): δ 41.49, 114.84, 118.29, 120.75, 127.24, 127.55, 128.66, 128.90, 129.05, 131.53, 136.54, 137.69, 157.24.

19b: 2-(benzylthio)phenyl-N-methylcarbamate. White crystalline solid; 78% yield; 1H NMR (CDCl$_3$): δ 2.92 (d, J=5.00 Hz, 3H), 4.08 (s, 2H), 4.99 (s, 1H), 7.12-7.32 (m, 9H); 13C NMR (CDCl$_3$): δ 27.93, 38.21, 123.03, 126.12, 127.34, 127.63, 128.57, 129.07, 129.75, 131.02, 137.19, 149.68, 154.79; HRMS (FAB): 274.09018 calcd for C$_{15}$H$_{15}$NO$_2$S [M+H]$^+$ found 274.09119 (3.7 ppm, 1.0 mmu).

EXAMPLE XXVI

20b: 2-(2-methylallyloxy)phenyl-N-methylcarbamate. White crystalline solid; 74% yield; 1H NMR (CDCl$_3$): δ 1.81 (s, 3H), 2.87 (d, J=4.95 Hz, 3H), 4.45 (s, 2H), 4.96 (s, 1H), 5.09 (s, 2H), 6.91-6.94 (m, 2H), 7.09-7.15 (m, 2H); 13C NMR (CDCl$_3$): δ 19.33, 27.88, 72.30, 112.53, 113.86, 121.01, 123.37, 126.39, 140.48, 140.69, 150.96, 155.15; HRMS (FAB): 222.11302 calcd for C$_{12}$H$_{15}$NO$_3$ [M+H]$^+$ found 222.11441 (6.2 ppm, 1.4 mmu).

EXAMPLE XXVII

21p: 2-(2-bromoallyloxy)phenol. This compound was prepared in 52% yield from catechol and 2-bromoallyl bromide according to the procedure for 2p in Example IX. Yellow oil; 1H NMR (CDCl$_3$): δ 4.70 (s, 2H), 5.68 (s, 1H), 5.70-5.71 (m, 1H), 5.95-5.96 (m, 1H), 6.81-6.97 (m, 4H); 13C NMR (CDCl$_3$): δ 73.10, 113.09, 115.33, 119.17, 120.28, 122.82, 127.06, 144.83, 146.12; HRMS (FAB): 243.95575 calcd for C$_9$H$_9$BrOS [M]$^+$ found 243.9557 (−0.2 ppm, 0.0 mmu).

21b: 2-(2-bromoallyloxy)phenyl-N-methylcarbamate. Pale oil; 31% yield; 1H NMR (CDCl$_3$): δ 2.89 (d, J=4.95 Hz, 3H), 4.65 (s, 2H), 5.02 (s, 1H), 5.65 (d, J=1.95 Hz, 1H), 6.02 (d, J=1.5 Hz, 1H), 6.91 (d, J=8.00 Hz, 1H), 6.97 (t, J=7.70 Hz, 1H), 7.11 (d, J=7.95 Hz, 1H), 7.15 (t, J=9.05 Hz, 1H); 13C NMR (CDCl$_3$): δ 28.00, 72.24, 114.34, 117.77, 122.04, 123.62, 123.72, 126.48, 126.58, 140.54, 155.03; HRMS (FAB): 286.00789 calcd for C$_{11}$H$_{12}$BrNO$_3$ [M+H]$^+$ found 286.00626 (−5.6 ppm, −1.6 mmu).

EXAMPLE XXVIII

22b: 2-isopropylphenyl-N-methylcarbamate. Yellow solid; 80% yield; 1H NMR (CDCl$_3$): δ 1.21 (d, J=6.90 Hz, 6H), 2.88 (d, J=4.95 Hz, 3H), 3.12 (s-7, J=6.85 Hz, 1H), 5.05 (s, 1H), 7.04-7.07 (m, 1H), 7.17-7.19 (m, 2H), 7.28-7.30 (m, 1H); 13C NMR (CDCl$_3$): δ 23.10, 27.33, 27.890, 122.65, 125.97, 126.62, 140.72, 148.42, 155.59.

EXAMPLE XXIX

23b: 2-tert-butylphenyl methylcarbamate. White solid; 67% yield; 1H NMR (CDCl$_3$): δ 1.36 (s, 9H), 2.93 (d, J=4.95 Hz, 3H), 5.03 (s, 1H), 7.05 (dd, J=1.35 Hz, J=7.95 Hz, 1H), 7.14 (dt, J=1.35 Hz, J=7.95 Hz, 1H), 7.22 (dt, J=1.65 Hz, J=7.70 Hz, 1H), 7.37 (dd, J=1.65 Hz, J=7.97 Hz, 1H); 13C NMR (CDCl$_3$): δ 27.90, 30.32, 34.63, 124.20, 125.34, 126.94, 127.05, 141.34, 149.67, 155.36; HRMS (FAB): 208.13376 calcd for C$_{12}$H$_{17}$NO$_2$ [M+H]$^+$ found 208.1342 (2.1 ppm, 0.4 mmu).

EXAMPLE XXX

8c: 2-(3-thio-2-methylpropenyl)phenyl-N-ethylcarbamate. A 25 mL round-bottom flask was charged with 8p (0.198 g, 1.10 mmol), THF (10 mL) and purged with nitrogen. Diisopropylethylamine (0.2 mL, 1.15 mmol, 1.05 equiv). was added via syringe followed by ethyl isocyanate (3.5 mL, 44.56 mmol, 40.6 equiv). After 4 h, the reaction was diluted with CH$_2$Cl$_2$ (60 mL), washed successively with 0.25 M HCl (2×60 mL), water (3×60 mL) and brine (60 mL). After drying over MgSO$_4$ (anhydrous), the solution was filtered, concentrated in vacuo, and the residue was purified by flash (15% ethyl acetate/hexane) to afford the desired product as a colorless oil, 202.5 mg, 0.806 mmol (73% yield). 1H NMR (CDCl$_3$): δ 1.18 (t, $^3$J=7.2 Hz, 3H, major amide conformer, CH$_2$CH$_3$), 1.24 (br.t, shoulder to triplet at δ 1.18, $^3$J=6.8 Hz, 3H, minor amide conformer, CH$_2$CH$_3$), 1.82 (d, $^4$J=0.8 Hz, 3H, C=CCH$_3$), 3.29 (quintet, $^3$J=6.9 Hz, major amide conformer, 2H, NHCH$_2$CH$_3$), 3.40 (m, shoulder to singlet at δ 3.44, minor amide conformer, 2H, NHCH$_2$CH$_3$), 3.44 (s, 2H, SCH$_2$), 4.78 (d, $^4$J=1.2 Hz, 1H, C=CH), 4.81 (d, $^4$J=0.8 Hz, 1H, C=CH'), 5.11 (br.s, 1H, NH), 7.09-7.13 (m, 2H, Ar), 7.16-7.23 (m, 1H, Ar), 7.30-7.32 (m, 1H, Ar) ppm; $^{13}$C NMR (CDCl$_3$): δ 15.08, 21.19, 36.21, 40.92, 114.21, 122.89, 125.84, 127.31, 129.62, 131.07, 140.49, 149.72, 153.92 ppm; HRMS (FAB+, Direct) m/z calcd for C$_{13}$H$_{18}$NO$_2$S (M+H$^+$) 252.1058, found 252.1054 (100%).

EXAMPLE XXXI 8d 2-(3-thio-2-methylpropenyl)phenyl-N-hexylcarbamate. This compound was prepared from 8p and hexyl isocyanate in 47% yield according to the procedure for 8c. Colorless oil; 1H NMR (CDCl$_3$): δ 0.90 (t, $^3$J=5.5 Hz, 3H, hexyl CH$_3$), 1.28-1.40 (m, 6H, hexyl CH$_2$), 1.57 (quintet, $^3$J=5.8 Hz, 2H, NCH$_2$CH$_2$), 1.85 (d, $^4$J=0.6 Hz, 3H, C=CCH$_3$), 3.27 (q, $^3$J=6.7 Hz, major amide conformer, 2H, NHCH$_2$CH$_2$), 3.36-3.41 (m, minor amide conformer, 2H, NHCH$_2$CH$_3$), 3.48 (s, 2H, SCH$_2$), 4.82 (d, $^4$J=1.4 Hz, 1H, C=CH), 4.84 (s, 1H, C=CH'), 5.13 (br.s, 1H, NH), 7.12-7.16 (m, 2H, Ar), 7.19-7.22 (m, 1H, Ar), 7.34-7.35 (m, 1H, Ar) ppm; 13C NMR (CDCl$_3$): δ 13.98, 21.19, 22.53, 26.34, 29.75, 31.42, 40.92, 41.33, 114.20, 122.90, 125.82, 127.30, 129.64, 131.04, 140.48, 149.74, 154.04 ppm; HRMS (FAB+, Direct) m/z calcd for C$_{17}$H$_{26}$NO$_2$S (M+H$^+$) 308.1684, found 308.1688 (100%).

EXAMPLE XXXII

8e: 2-(3-thio-2-methylpropenyl)phenyl-N,N-dimethylcarbamate. This compound was prepared in 97% yield from 8p and N,N-dimethylcarbamoyl chloride using the general procedure for 16b in Example VII. Colorless oil; 1H NMR (CDCl$_3$): δ 1.82 (s, 3H, CH$_3$), 2.99 (s, 3H, NCH$_3$), 3.13 (s, 3H, NC'H$_3$), 3.44 (s, 2H, SCH$_2$), 4.78 (d, $^4$J=0.8 Hz, 1H, C=CH), 4.81 (~s, 1H, C=CH'), 7.08-7.13 (m, 2H, Ar), 7.16-7.23 (m, 1H, Ar), 7.30-7.32 (m, 1H, Ar); 13C NMR (100 MHz, CDCl$_3$): δ 21.21, 36.49, 36.80, 40.97, 114.14, 122.93, 125.73, 127.27, 129.45, 130.98, 140.52, 150.23, 154.29 ppm; HRMS (FAB+, Direct) m/z calcd for C$_{13}$H$_{18}$NO$_2$S (M+H$^+$) 251.0980, found 252.1047 (100%).

Mosquito rearing and toxicity tests. The G3 strain of *Anopheles gambiae*, originally obtained from MR4, the Malaria Research and Reference Reagent Resource Center, was used in all toxicity tests. The genotype is wild type and the phenotype is wild type, insecticide-susceptible S form of *Anopheles gambiae*. Filter paper assays were performed to measure contact toxicity. Tests were run in exposure tubes according to W.H.O. (1981) methods. (WHO. 1981. Instructions for determining the susceptibility or resistance of adult mosquitoes to organochlorine, organophosphate and carbamate insecticides: Establishment of the base-line. Document WHO/VBC/81.805. World Health Organization, Geneva.) Batches of 15-20 non-blood fed females, 3-5 days old, were placed in the holding tube for a 1-hour adaptation period. They were then transferred to the exposure tube containing treated filter paper and held vertically for 1 hour at 27° C. and 80% RH. Knockdown was determined by counting the number of incapacitated mosquitoes at the bottom on the tubes at 10-minute intervals. After 1 hour, the mosquitoes were transferred to the holding tube and held for 24 hours with access to sugar water and mortality was recorded.

Dilutions of candidate insecticidal carbamates were prepared in 95% ethanol or 99% dichloromethane, depending on the solubility of the test compound. Filter papers (15×12 cm) were impregnated with 2 mL of each dilution and dried for 24 hours before testing. Insecticide concentrations are reported as ug/cm$^2$. The negative control was either 95% ethanol or 99% dichloromethane; 0.1% (w/v) Propoxur provided the positive control (final concentration 11 ug/cm$^2$). To evaluate the synergistic effects of inhibiting cytochrome P450 oxidative metabolism of the insecticides, in select cases, piperonyl butoxide (PBO) (0.3 mg/mL) was incorporated in the insecticide solution before dispersal on the filter paper. (Paul, A.; Harrington, L. C.; Scott, J. G. Evaluation of novel insecticides for control of dengue vector *Aedes aegypti* (Diptera: Culicidae). *J. Med. Entomol.* 2006, 43, 55-60.) To calculate LC$_{50}$ values, data were pooled and analyzed by standard probit analysis (Finney, D. J. *Probit Analysis*. Cambridge University Press: Cambridge, England, 1971) using PoloPlus (Robertson, J. L, H. K. Preisler, and R. M. Russell. 2002. PoloPlus Probit and Logit Analysis. LeOra Software).

Protein expression. A DNA sequence encoding the entire wild type AgAChE protein (acel, 737 amino acids) was synthesized and cloned (GenScript Co., Piscataway, N.J.). This sequence was derived from the AgAChE sequence in the Ensembl database (www.ensembl.org) and spanned 18 nucleotides upstream of the start codon to the amino acid codon preceding the stop codon (nt 210 to 2438, Accession # XM_321792). The encoded amino acid sequence differs from that reported by Weill et al. at two amino acid positions (Weill, M.; Malcolm, C.; Chandre, F.; Mogenson, K.; Berthomieu, A.; Marquine, M.; Raymond, M. The unique mutation in ace-1 giving high insecticide resistance is easily detectable in mosquito vectors. *Insect Mol. Biol.* 2004, 13, 1-7). At amino acid positions 35 and 65, there are serines in the Weill et al. (Weill, 2004) sequence and phenylalanine and alanine, respectively, in the Ensembl sequence. Expression of recombinant AgAChE utilized the *Drosophila* Expression System (Invitrogen, Carlsbad, Calif.). Briefly, the AgAChE cDNA was cloned into the expression vector pMT/V5-His in the absence of a stop codon to generate a fusion protein consisting of the AgAChE-V5 epitope-6×His tag. Stably transfected *Drosophila* S2 cells were selected by cotransfection with the pCoBlast vector in the presence of blastocidin (25 ug/ml). S2 cells were routinely grown in Schneider's *Drosophila* medium. For preparation of cell lysates, stably transfected S2 cells were grown in suspension in spinner flasks and induced with 1 mM copper sulfate. Following 48 hrs of induction at room temperature, the cells were collected by centrifugation. The cell pellet was resuspended in lysis buffer containing 50 mM NaH$_2$PO$_4$ (pH 8.0), 0.5 M NaCl, 1% NP-40 and a cocktail of protease inhibitors (1.4 uM pepstatin, 0.3 uM aprotinin, 1 uM leupeptin, 1 mM EDTA). Following a 15 minute incubation at 4° C. with gentle agitation, the cell lysate was centrifuged at 3,000×g for 15 minutes. The clear supernatant was collected and used for enzymatic assays. As used in the context of this application, this protein is referred to as "Ag ace-1S" to represent that it is the insecticide-susceptible AgAChE enzyme encoded by ace-1.

Enzyme inhibition assays. Inhibition of AChE (Ag homogenate, Ag ace-1S and hAChE) was determined at pH 7.8 using the Ellman assay in a microtiter plate format. (Ellman, G. L.; Courtney, K. D.; Andres, V. J.; Featherstone, R. M. A new and rapid colorimetric determination of acetylcholinesterase activity. *Biochem. Pharm.* 1961, 7, 88-95.) Enzyme preparations were incubated with inhibitors for 10 minutes prior to addition of DTNB and acetylthiocholine (ATCh). The final concentrations of DTNB and ATCh are 0.3 and 0.4 mM, respectively. Five inhibitor concentrations (run in quadruplicate) were used to construct dose-response curves (Prism 4 for Macintosh).

The total volume in each well of the microtiter plate was 200 uL; the enzyme preparation comprised 10 uL in each case. To prepare the Ag homogenate (Ag hmg) 10 *Anopheles gambiae* mosquitoes were combined with 1 mL ice-cold 0.1 M Na$_2$HPO$_4$ buffer (adjusted with 0.1 M NaH$_2$PO$_4$ to pH 7.8) containing 0.1% Triton X-100 in a glass homogenizer. The crude homogenate was then centrifuged for 10 min at 4° C. in a microcentrifuge, and the supernatant was transferred to a clean 1.5 mL microcentrifuge tube and stored on ice prior to use. Recombinant AgAChE (Ag ace-1S described above) was obtained in the form of a centrifuged cell lysate and diluted 10:1 with buffer prior to use. Recombinant hAChE (lyophilized powder, Sigma C1682) with a quoted specific activity of 2790 units/mg was diluted to 600 U/mL with buffer, frozen, and stored at −80° C. Immediately prior to assay, a frozen hAChE sample was thawed and diluted 1000-fold with buffer before use.

AChE inhibition of seven common commercial carbamate insecticides at three enzyme sources (Ag hmg, Ag ace-1S, and hAChE) were examined. As can be seen in Table 1, $IC_{50}$ values of these seven commercial carbamates are similar at Ag hmg and Ag ace-1S, suggesting that Ag ace-1S is the major ATCh-hydrolyzing enzyme present in the Ag hmg. AChE inhibition of the following carbamates were examined:

TABLE 1

Low *Anopheles gambiae*/human selectivity of AChE inhibition by common insecticidal carbamates

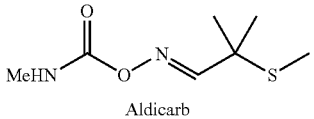

Aldicarb

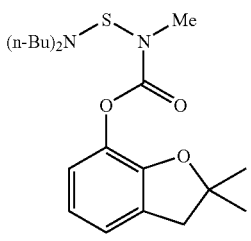

Carbosulfan

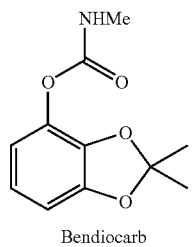

Bendiocarb

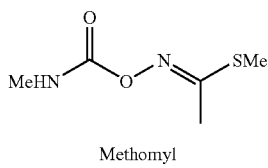

Methomyl

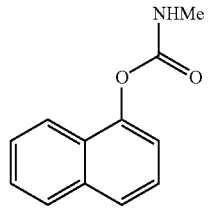

Carbaryl

TABLE 1-continued

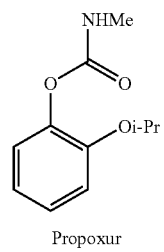

Propoxur

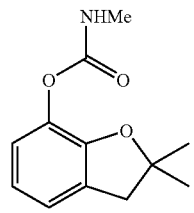

Carbofuran

| Insecticide | hAChE recomb $IC_{50}$ (nM) | Ag hmg[a] $IC_{50}$ (nM) | Ag ace-1S[b] $IC_{50}$ (nM) | Live Mosquito Contact Toxicity MC (ug/cm$^2$) for 100% lethality at 24 hr[c] |
|---|---|---|---|---|
| Aldicarb | 4,421 | 4624 (0.95x) | 10,890 (0.41x) | 0.55 |
| Bendiocarb | 270 | 65 (4.1x) | 142 (1.9x) | 0.55 |
| Carbaryl | 2,844 | 262 (11x) | 515 (5.5x) | 2.7 |
| Carbofuran | 61 | 22 (2.8x) | 49 (1.2x) | 0.55 |
| Carbosulfan | 5,920 | 4,099 (1.4x) | 10,850 (0.54x) | 1.1 |
| Methomyl | 626 | 716 (0.87x) | 1,762 (0.36x) | 2.7 |
| Propoxur | 444 | 371 (1.2x) | 213 (2.1x) | 1.1 |

[a]Enzyme source is WT *Anopheles gambiae* homogenate; values in parenthesis are $IC_{50}$ ratios (hAChE/Ag hmg).
[b]Enzyme source is recombinant *Anopheles gambaie* AChE, WT (susceptible) strain; values in parenthesis are $IC_{50}$ ratios (hAChE/Ag ace-1S).
[c]Minimum concentration (ug/cm$^2$) to cause 100% lethality of *Anopheles gambiae* at 24 h under standard WHO contact toxicity conditions (1 hr exposure to treated filter paper).

As can be seen, selectivity for AgAChE over hAChE inhibition is low with these compounds. The most selective compound is Carbaryl, which ranges from 5.5-11-fold selective.

Carbamates of Formula (I). We then prepared a range of 3-substituted phenyl N-methylcarbamates 1a-13a conforming to the following general formula:

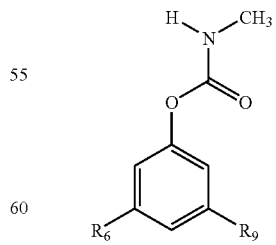

We assayed compounds having various substituents, $R_9$ and $R_6$, in the three enzyme screen. The compounds tested and their corresponding results are provided in Table 2.

TABLE 2

| Compound | $R_9$ | $R_6$ | hAChE recomb. $IC_{50}$ (nM) | Ag WT hmg[a] $IC_{50}$ (nM) | Ag ace-1S[b] $IC_{50}$ (nM) | Live Mosquito Contact Toxicity MC (ug/cm$^2$) for 100% lethality at 24 hr[c] |
|---|---|---|---|---|---|---|
| 1a | t-Bu | H | 265 | 3.1 (85x) | 7 (38x) | 1.1 (0.28) |
| 2a | SiMe$_3$ | H | 532 | 5.6 (95x) | 4.1 (130x) | 5.6 (80% lethal at 2.8) |
| 3a | SiEtMe$_2$ | H | 285 | 2.7 (110x) | 2.2 (130x) | 11 (60% lethal at 2.8) |
| 4a | i-Pr | H | 157 | 27 (5.8) | 12 (13x) | 56 |
| 5a | Et | H | 2,500 | 630 (4.0) | 392 (6.4x) | 11 |
| 6a | Ph | H | 38,880 | 18,350 (2.1x) | 12,080 (3.2x) | 56 |
| 7a | Cl | H | 86,000 | 26,000 (3.3x) | 16590 (5.2x) | 56 |
| 8a | Br | H | >100,000 | 23,970 (>4.2x) | 7607 (>13x) | 11 |
| 9a | I | H | 67,200 | 5,169 (13x) | 1822 (37x) | 11 |
| 10a | Me | Me | 17,410 | 2,778 (6.2x) | 1,040 (17x) | 56 |
| 11a | t-Bu | t-Bu | 5,166 | 5,318 (1.0x) | 2,469 (2.1x) | None at 11 |
| 12a | CF$_3$ | F | >100,000 | >100,000 (na) | 78,480 (na) | None at 11 |
| 13a | 1-benzyl-triazol-4-yl | H | >100,000 | 336,000 (na) | nd | None at 11 |

[a]Enzyme source is *Anopheles gambiae* homogenate; values in parenthesis are $IC_{50}$ ratios (hAChE/Ag hmg); na means not applicable, because the ratio cannot be determined.
[b]Enzyme source is recombinant *Anopheles gambaie* AChE, WT (susceptible) strain; values in parenthesis are $IC_{50}$ ratios (hAChE/Ag ace-1S); nd means not determined.
[c]Minimum concentration (ug/cm$^2$) to cause 100% lethality of *Anopheles gambiae* at 24 h under standard WHO contact toxicity conditions (1 hr exposure to treated filter paper). Values in parenthesis represent data in the presence of a synergist (piperonyl butoxide 0.3 mg/mL). Compounds causing no lethality at 24 h are labeled "none" and the highest concentration tested is given.

As shown in Table 2, Ag hmg $IC_{50}$ values are quite similar to those obtained with the recombinant Ag ace-1S. FIG. 1 provides a plot of log(Ag ace-1S $IC_{50}$ (nM)) vs log(Ag hmg $IC_{50}$ (nM)) for all the commercial and synthesized inhibitors described in Tables 1 and 2. The r$^2$ value of 0.937 provides further confirmation that the major ATCh-hydrolyzing enzyme in the Ag hmg is ace-1S.

The most striking feature to emerge in Table 2, however, is the highly potent and selective AgAChE inhibition obtained with inhibitors 1a-3a. Human/Ag $IC_{50}$ ratios range from 38 to 130-fold based on recombinant Ag ace-1S, and 85 to 110-fold based on Ag hmg data. The contact toxicity of these inhibitors was also excellent. In the presence of synergist piperonyl butoxide, a one hour exposure to filter paper treated with carbamate 1a at 0.28 ug/cm$^2$ kills 100% of *Anopheles gambaie* within 24 hours. Similarly, one hour exposure to filter paper treated with 2a and 3a at 2.8 ug/cm$^2$ kills 80 and 60% of Ag mosquitoes within 24 hours.

The present inventors have, thus, identified that the substituent at C3 plays a role in AgAChE potency and selectivity. Interestingly, as the size of the 3-alkyl group is decreased from t-Bu (1a) to i-Pr (4a) to Et (5a), both AgAChE inhibition potency and selectivity decrease significantly. Lower inhibition potency is also seen for 3-phenyl (6a) and 3-halo (7a-9a) substituted carbamates, although the 3-iodo substituted carbamate 9a offers significant selectivity. Keeping the 3-t-butyl group constant, carbamates 1c-1h were prepared to assess the effect of the N-alkyl group on AChE inhibition potency (Table 3).

TABLE 3

Variation of N-alkyl group

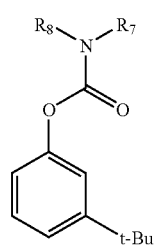

| Compound | $R_7$ | $R_8$ | hAChE recomb. $IC_{50}$ (nM) | Ag WT hmg[a] $IC_{50}$ (nM) | Live Mosquito Contact Toxicity MC for 100% leathality at 24 hr[b] |
|---|---|---|---|---|---|
| 1a | Me | H | 265 | 3.1 | 1.1 (0.28) |
| 1h | Et | H | 2,408 | 3,997 | 11 |
| 1c | n-hexyl | H | 696 | >100,000 | 13% lethal at 11 |

TABLE 3-continued

Variation of N-alkyl group

[Chemical structure: phenyl N-carbamate with R7, R8 on nitrogen and t-Bu substituent on ring]

| Compound | R7 | R8 | hAChE recomb. IC$_{50}$ (nM) | Ag WT hmg$^a$ IC$_{50}$ (nM) | Live Mosquito Contact Toxicity MC for 100% leathality at 24 hr$^b$ |
|---|---|---|---|---|---|
| 1d | i-Pr | H | 181,000 | 538,000 | None at 11 |
| 1e | Propargyl | H | 205 | 339 | 56 |
| 1f | (1-benzyl-triazol-4-yl)methyl | H | >10,000 | >10,000 | 56 |
| 1g | Me | Me | 4,036 | 5,945 | 20% lethal at 11 |

$^a$Enzyme source is WT *Anopheles gambiae* homogenate; values in parenthesis are IC$_{50}$ ratios (hAChE/Ag WT).
$^b$Minimum concentration (ug/cm$^2$) to cause 100% lethality of *Anopheles gambiae* at 24 h under standard WHO contact toxicity conditions (1 hr exposure to treated filter paper). Values in parenthesis represent data in the presence of a synergist (piperonyl butoxide 0.3 mg/mL).

As can be seen, AgAChE inhibition is sensitive to the nature of the N1-alkyl group. A methyl group (1a) gives the highest inhibition potency, as has been seen in numerous previous studies of *Musca domestica* (i.e. housefly) AChE (MdAChE). (Kolbezen, 1954 and Metcalf, 1971.)

As Table 4 illustrates, however, carbamate 1a is much more potent at Ag hmg AChE (3 nM) than at Md homogenate AChE (400 nM). This >100-fold difference in potency for two insect species is unanticipated and leads to the 85-fold selectivity for Ag hmg AChE relative to hAChE noted above in Table 2.

TABLE 4

Comparison of Ag homogenate and Md head homogenate (Metcalf 1971) IC$_{50}$ values

| Compound | R9 | R6 | Ag WT hmg$^a$ IC$_{50}$ (nM) | Md WT hmg$^b$ IC$_{50}$ (nM) |
|---|---|---|---|---|
| 1a | t-Bu | H | 3.1 | 400 |
| 2a | SiMe$_3$ | H | 5.6 | 700 |
| 4a | i-Pr | H | 27 | 340 |
| 5a | Et | H | 630 | 13,000 |
| 7a | Cl | H | 26,000 | 50,000 |
| 8a | Br | H | 23,970 | 13,000 |
| 9a | I | H | 5,169 | 7,000 |
| 10a | Me | Me | 2,778 | 6,000 |
| 11a | t-Bu | t-Bu | 5,318 | 78 |
| Aldicarb | Na | na | 4,624 | 84,000 |
| Carbaryl | Na | na | 262 | 900 |
| Propoxur | Na | na | 371 | 670 |

$^a$Enzyme source is *Anopheles gambiae* homogenate
$^b$Enzyme source is *Musca domestica* head homogenate; data from Metcalf.[8]

Similarly, carbamate 2a (2921-34-8) is reported to be a 700 nM inhibitor at Md hmg AChE. (Metcalf I 1965.) The 100-fold greater potency of 2a at Ag hmg AChE is again unexpected. A less dramatic but still significant enhancement in potency is seen for carbamate 4a: it is 340 nM at MdAChE, but 27 nM at AgAChE. (Metcalf II 1965.) Finally, not all the inhibitors in Table 4 are more potent at AgAChE than MdAChE. A dramatic reversal in inhibition potency is seen for 11a (tradename butacarb): it is 5,318 nM at Ag hmg AChE, but 78 nM at Md hmg AChE. (Metcalf II 1965.) Thus, as can be seen, neither MdAChE nor bovine AChE IC$_{50}$ values are predictive of AgAChE IC$_{50}$ values.

Consequently, the high selectivity shown by the present inventors for Ag relative to hAChE seen with inhibitors 1a-3a is unprecedented, could not have been predicted, and is thus non-obvious. The common structural feature these three inhibitors share is the presence of a trialkylmethyl or trialkylsilyl group at the meta-position of a phenyl N-methylcarbamate.

Carbamates of Formula (II). We then prepared a range of 2-substituted phenyl N-methylcarbamates 1b-23b, and assayed them in the three enzyme screen (Table 5).

TABLE 5

N-methyl carbamates

[Structure: phenyl N-methylcarbamate with R₁₂ substituent at ortho position]

| Compound | R₁₂ | hAChE recomb. IC$_{50}$ (nM) | Ag WT hmg[a] IC$_{50}$ (nM) | Ag ace-IS[b] IC$_{50}$ (nM) | Live mosquito toxicity MC (ug/cm$^2$) for 100% lethality at 24 hr[c] |
|---|---|---|---|---|---|
| 1b | ～S-CH₂-CH(Et)(Et) | 3630 | 3 (1210x) | 2.9 (1250x) | 27% at 11 |
| 2b | ～O-CH₂-CH(Et)(Et) | 98,820 | 69 (1,400x) | 10 (9,900x) | 27% at 11; 53% at 11 (+PBO) |
| 3b | ～S(=O)-CH₂-CH(Et)(Et) | 55,380 | 51,750 (1.1x) | nd | 0% at 11 |
| 4b | ～S-CH₂-CH(Me)(Et) | 3540 | 30 (118x) | 27 (131x) | 70 % at 11 |
| 5b | ～S-CH(Me)(Me) | 943 | 33 (29x) | nd | 2.8 |
| 6b | ～S-CH₂-CH(Me)(Me) | 8114 | 109 (74x) | nd | 11 |
| 7b | ～S-CH₂-C(Me)₃ | 13,940 | 732 (19x) | 287 (49x) | 33 % at 11 |
| 8b | ～S-CH₂-C(=CH₂)Me | 9,551 | 124 (77x) | 165 (58x) | 2.8 |

TABLE 5-continued
N-methyl carbamates
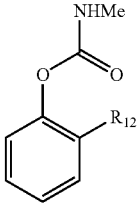
| Compound | $R_{12}$ | hAChE recomb. $IC_{50}$ (nM) | Ag WT hmg[a] $IC_{50}$ (nM) | Ag ace-IS[b] $IC_{50}$ (nM) | Live mosquito toxicity MC (ug/cm$^2$) for 100% lethality at 24 hr[c] |
|---|---|---|---|---|---|
| 9b  | 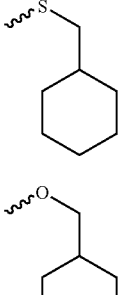 | 10,600   | 17,500 (0.61x) | nd        | nd |
| 10b | 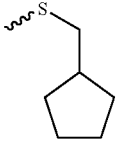 | >100,000 | >100,000       | nd        | nd |
| 11b | 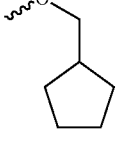 | 6,880    | 1,070 (6.2x)   | 391 (18x) | nd |
| 12b | 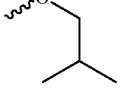 | >100,000 | 24,600 (4x)    | nd        | nd |
| 13b | 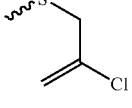 | 66,900   | 2,060 (32x)    | 650 (100x)| 100% at 2.8 |
| 14b | 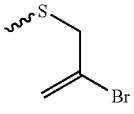 | 3,100    | 114 (27x)      | 264 (12x) | 11 |
| 15b | 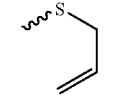 | 1,658    | 248 (6.7x)     | 173 (9.6x)| 93% lethal at 56 |
| 16b |  | 1,583    | 156 (10x)      | 36 (44x)  | 5.6 |

TABLE 5-continued

N-methyl carbamates

| Compound | R₁₂ | hAChE recomb. IC$_{50}$ (nM) | Ag WT hmg$^a$ IC$_{50}$ (nM) | Ag ace-1S$^b$ IC$_{50}$ (nM) | Live mosquito toxicity MC (ug/cm$^2$) for 100% lethality at 24 hr$^c$ |
|---|---|---|---|---|---|
| 17b | -S-CH₂-CH=CH-CH₃ | 494 | 57 (8.7x) | 68 (7.3x) | 93% lethal at 5.6 |
| 18b | -S-CH₂-C(CH₃)=CH₂ (prenyl) | 2,703 | 1,177 (2.3x) | 411 (6.6x) | 56 |
| 19b | -S-CH₂-Ph | 15,660 | 6,903 (2.3x) | 3,842 (4.1x) | None at 11 |
| 20b | -O-CH₂-C(CH₃)=CH₂ | 68,730 | 1,510 (46x) | nd | 93% lethaity at 11 |
| 21b | -O-CH₂-C(Br)=CH₂ | 31,850 | 1,068 (30x) | 741 (43x) | 11 |
| 22b (328) | i-Pr | 4,542 | 507 (8.8x) | 426 (11x) | 56 |
| 23b (330) | t-Bu | >100,000 | 79,000 (>1.3x) | 51,700 (1.9x) | 56 |

$^a$Enzyme source is WT *Anopheles gambiae* homogenate; values in parenthesis are IC$_{50}$ ratios (hAChE/Ag hmg).

$^b$Enzyme source is recombinant full-length *Anopheles gambaie* AChE, WT (susceptible) strain; values in parenthesis are IC$_{50}$ ratios (hAChE/Ag ace-1S).

$^c$Minimum concentration (ug/cm$^2$) to cause 100% lethality of *Anopheles gambiae* at 24 h under standard WHO contact toxicity conditions (1 hr exposure to treated filter paper). If all the mosquitoes do not die within 24 h, the % olethality at 24 h is given.

Figure 2:
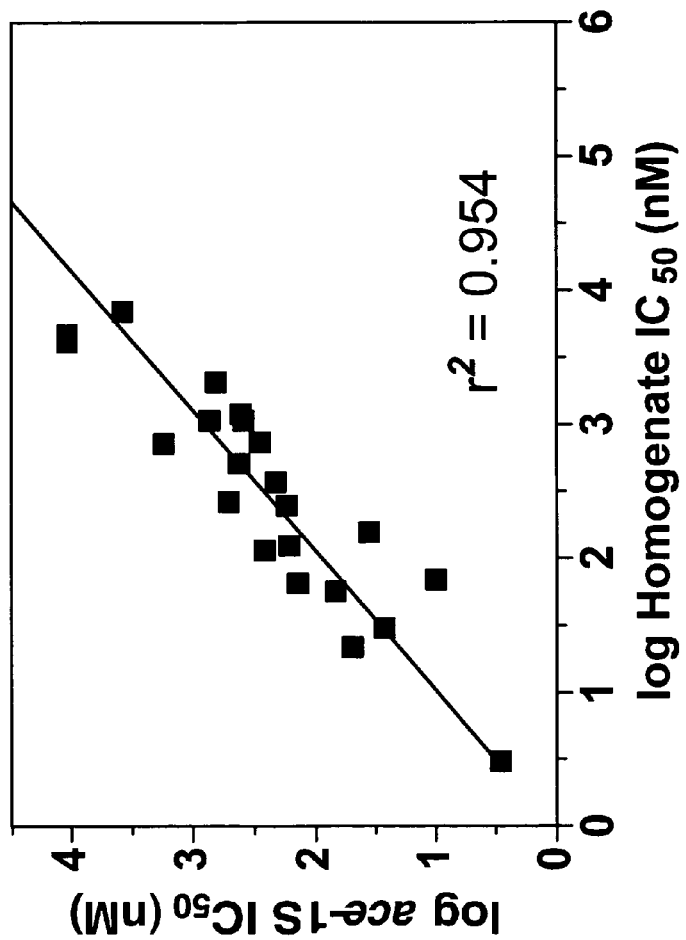
FIG. 2 is a graph showing a plot of log [Ag ace-1S $IC_{50}$] vs log [Ag hmg AChE $IC_{50}$] for the compounds in Tables 1 and 5.

As shown in Table 5, Ag hmg IC$_{50}$ values are quite similar to those obtained with the recombinant Ag ace-1S. FIG. 2 provides a plot of log [Ag ace-1S IC$_{50}$] vs log [Ag hmg AChE IC$_{50}$] for all the compounds in Tables 1 and 5. The r$^2$ value of 0.954 provides further confirmation that the major ATCh-hydrolyzing enzyme in the Ag hmg is ace-1S.

Figure 3:
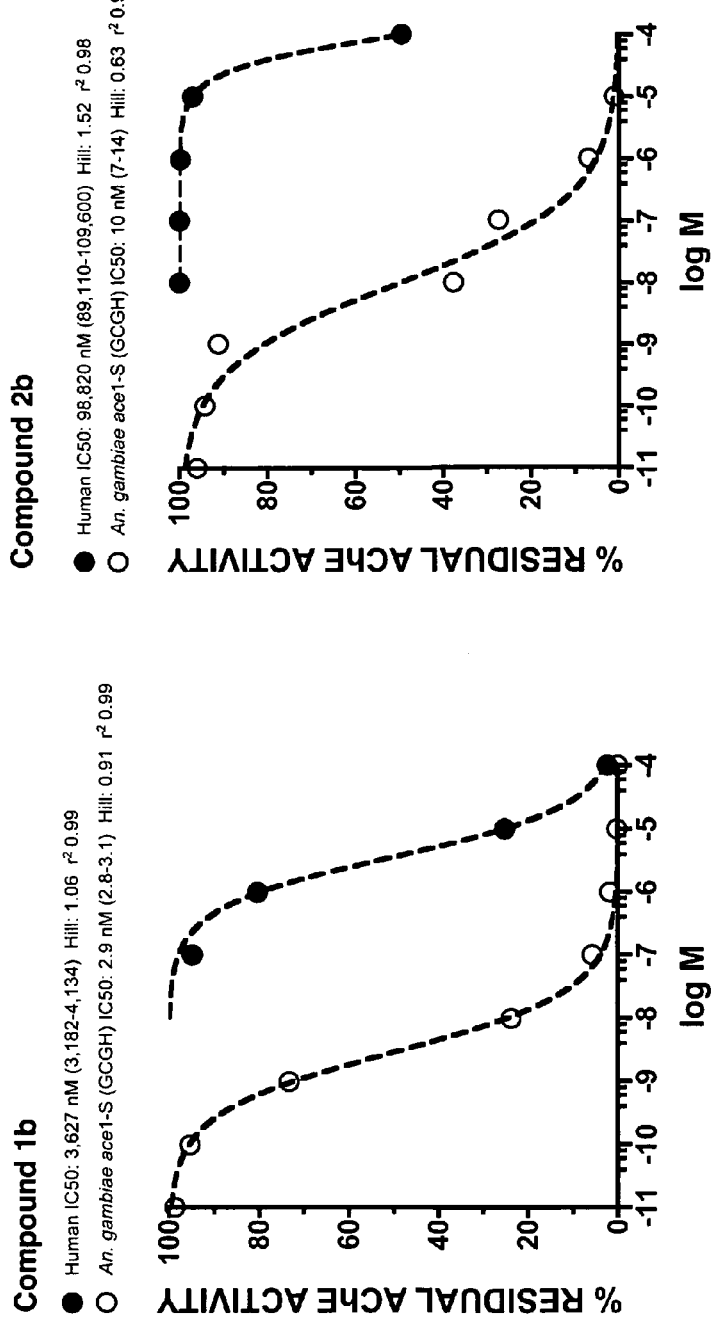
FIG. 3 shows graphs showing full dose-response curves for carbamates 1b and 2b.

The most striking feature to emerge in Table 5, however, is the highly potent and selective AgAChE inhibition obtained with carbamates 1b, 2b, 4b, 6b, 8b, and 13b. Because two sources of AgAChE are used, two independent measures of the selectivity are available for most compounds. Human/Ag IC$_{50}$ ratios of these highly selective carbamates range as follows: 58-to 77-fold for 8b; 74-fold for 6b; 32-to 100-fold for 13b; to 32-to 131-fold for 4b; 1200-fold for 1b; and 1,400-9,900-fold for 2b. Full dose-response curves for the two most selective inhibitors are shown in FIG. 3. As can be seen in FIG. 3, carbamates 1b and 2b achieve >90% inhibition of AgAChE at concentrations where hAChE undergoes no measurable inhibition.

To assess the effect of variation of the N-alkyl group on inhibition potency and selectivity, 3 analogues of 8b were prepared (Table 6). As can be seen, only the N-methyl derivative 8b possesses selectivity for AgAChE inhibition.

TABLE 6

Variation of N-alkyl group

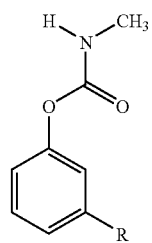

| Compound | R$_{10}$ | R$_{11}$ | hAChE recomb. IC$_{50}$ (nM) | Ag WT hmg$^a$ IC$_{50}$ | Live mosquito toxicity MC (ug/cm$^2$) for 100% lethality at 24 hr$^b$ |
|---|---|---|---|---|---|
| 8b | Me | H | 9,551 | 124 | 2.8 |
| 8c | Et | H | 54,220 | 12,950 | None at 11 |
| 8d | n-C6H13 | H | 6,858 | >100,000 | None at 11 |
| 8e | Me | Me | 10,330 | 5,821 | None at 11 |

$^a$Enzyme source is WT *Anopheles gambiae* homogenate; values in parenthesis are IC$_{50}$ ratios (hAChE/Ag hmg).
$^b$Minimum concentration (ug/cm$^2$) to cause 100% lethality of *Anopheles gambiae* at 24 h under standard WHO contact toxicity conditions (1 hr exposure to treated filter paper). If all the mosquitoes do not die within 24 h, the % lethality at 24 h is given.

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Other embodiments of the invention will be apparent to those skilled in the art from consideration of the specification and practice of the invention. The description of the invention provided is merely exemplary in nature and, thus, variations that do not depart from the essence of the invention are intended to be within the scope of the invention.

The invention claimed is:

1. A compound of Formula (I):

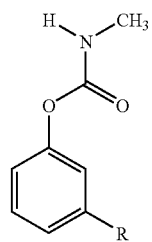

Formula (I)

wherein said compound is chosen from at least one of 3-(1,1,1-trifluoro-2-methylpropan-2-yl)phenyl N-methylcarbamate; 3-(1,1,1,3,3,3-hexafluoro-2-methylpropan-2-yl)phenyl N-methylcarbamate; 3-(1,1,1,3,3,3-hexafluoro-2-(trifluoromethyl)propan-2-yl)phenyl N-methylcarbamate; 3-(1,1,1-trifluoro-2-methylbutan-2-yl)phenyl N-methylcarbamate; 3-(1,1,1-trifluoro-2-(trifluoromethyl)butan-2-yl)phenyl N-methylcarbamate; 3-(3,3,4,4,4-pentafluoro-2-methylbutan-2-yl)phenyl N-methylcarbamate; 3-(1,1,1,3,3,4,4,4-octafluoro-2-methylbutan-2-yl)phenyl N-methylcarbamate; and 3-(1,1,1,3,3,4,4,4-octafluoro-2-(trifluoromethyl)butan-2-yl)phenyl N-methylcarbamate.

2. A method of making a compound of Formula (I) comprising:
deprotonating a phenol with K(Ot-Bu) or NaH in THF to obtain a deprotonated phenol;
carbamoylating said deprotonated phenol by reacting said deprotonated phenol with N-methyl carbamoyl chloride; and
isolating the resultant compound to obtain a compound of Formula (I):

Formula (I)

wherein said compound is chosen from at least one of 3-(1,1,1-trifluoro-2-methylpropan-2-yl)phenyl N-methylcarbamate; 3-(1,1,1,3,3,3-hexafluoro-2-methylpropan-2-yl)phenyl N-methylcarbamate; 3-(1,1,1,3,3,3-hexafluoro-2-(trifluoromethyl)propan-2-yl)phenyl N-methylcarbamate; 3-(1,1,1-trifluoro-2-methylbutan-2-yl)phenyl N-methylcarbamate; 3-(1,1,1-trifluoro-2-(trifluoromethyl)butan-2-yl)phenyl N-methylcarbamate; 3-(3,3,4,4,4-pentafluoro-2-methylbutan-2-yl)phenyl N-methylcarbamate; 3-(1,1,1,3,3,4,4,4-octafluoro-2-methylbutan-2-yl)phenyl N-methylcarbamate; and 3-(1,1,1,3,3,4,4,4-octafluoro-2-(trifluoromethyl)butan-2-yl)phenyl N-methylcarbamate.

3. A method of controlling mosquitoes comprising applying a compound lethal to mosquitoes to a substrate and exposing said substrate to mosquitoes for a time sufficient to kill said mosquitoes, wherein said compound is a compound of Formula (I):

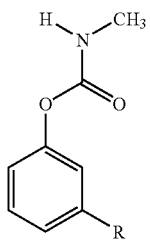

Formula (I)

wherein said compound is chosen from at least one of 3-(1,1,1-trifluoro-2-methylpropan-2-yl)phenyl N-methylcarbamate; 3-(1,1,1,3,3,3-hexafluoro-2-methylpropan-2-yl)phenyl N-methylcarbamate; 3-(1,1,1,3,3,3-hexafluoro-2-(trifluoromethyl)propan-2-yl)phenyl N-methylcarbamate; 3-(1,1,1-trifluoro-2-methylbutan-2-yl)phenyl N-methylcarbamate; 3-(1,1,1-trifluoro-2-(trifluoromethyl)butan-2-yl)phenyl N-methylcarbamate; 3-(3,3,4,4,4-pentafluoro-2-methylbutan-2-yl)phenyl N-methylcarbamate; 3-(1,1,1,3,3,4,4,4-octafluoro-2-methylbutan-2-yl)phenyl N-methylcarbamate; and 3-(1,1,1,3,3,4,4,4-octafluoro-2-(trifluoromethyl)butan-2-yl)phenyl N-methylcarbamate.

4. An insecticidal composition comprising a compound of Formula (I):

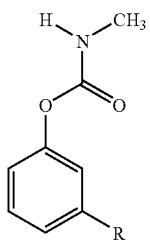

Formula (I)

wherein said compound is chosen from at least one of 3-(1,1,1-trifluoro-2-methylpropan-2-yl)phenyl N-methylcarbamate; 3-(1,1,1,3,3,3-hexafluoro-2-methylpropan-2-yl)phenyl N-methylcarbamate; 3-(1,1,1,3,3,3-hexafluoro-2-(trifluoromethyl)propan-2-yl)phenyl N-methylcarbamate; 3-(1,1,1-trifluoro-2-methylbutan-2-yl)phenyl N-methylcarbamate; 3-(1,1,1-trifluoro-2-(trifluoromethyl)butan-2-yl)phenyl N-methylcarbamate; 3-(3,3,4,4,4-pentafluoro-2-methylbutan-2-yl)phenyl N-methylcarbamate; 3-(1,1,1,3,3,4,4,4-octafluoro-2-methylbutan-2-yl)phenyl N-methylcarbamate; and 3-(1,1,1,3,3,4,4,4-octafluoro-2-(trifluoromethyl)butan-2-yl)phenyl N-methylcarbamate.

5. A net for controlling mosquitoes comprising a compound of Formula (I):

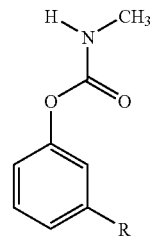

Formula (I)

wherein said compound is chosen from at least one of 3-(1,1,1-trifluoro-2-methylpropan-2-yl)phenyl N-methylcarbamate: 3-(1,1,1,3,3,3-hexafluoro-2-methylpropan-2-yl)phenyl N-methylcarbamate; 3-(1,1,1,3,3,3-hexafluoro-2-(trifluoromethyl)propan-2-yl)phenyl N-methylcarbamate; 3-(1,1,1-trifluoro-2-methylbutan-2-yl)phenyl N-methylcarbamate; 3-(1,1,1-trifluoro-2-(trifluoromethyl)butan-2-yl)phenyl N-methylcarbamate; 3-(3,3,4,4,4-pentafluoro-2-methylbutan-2-yl)phenyl N-methylcarbamate; 3-(1,1,1,3,3,4,4,4-octafluoro-2-methylbutan-2-yl)phenyl N-methylcarbamate; and 3-(1,1,1,3,3,4,4,4-octafluoro-2-(trifluoromethyl)butan-2-yl)phenyl N-methylcarbamate.

6. The method according to claim 3, wherein said applying comprises applying said compound of Formula (I) to agricultural substrates.

7. The method according to claim 3, wherein said applying comprises indoor residual spraying of said compound of Formula (I) or treating nets to obtain a net treated with an insecticide of Formula (I).

8. The insecticidal composition according to claim 4 further comprising a synergist for increasing lethality of said compound of Formula (I).

9. The net according to claim 5 further comprising a synergist for increasing lethality of said compound of Formula (I).

10. The insecticidal composition according to claim 8, wherein said synergist is piperonyl butoxide.

11. The net according to claim 9, wherein said synergist is piperonyl butoxide.

12. The compound according to claim 1 which exhibits selectivity for AgAChE over hAChE inhibition.

* * * * *